United States Patent
Khan et al.

(10) Patent No.: US 10,876,092 B2
(45) Date of Patent: Dec. 29, 2020

(54) METHOD FOR ADAPTATION

(71) Applicant: METABOGEN AB, Gothenburg (SE)

(72) Inventors: Muhammad-Tanweer Khan, Mölndal (SE); Fredrik Backhed, Kullavik (SE)

(73) Assignee: METABOGEN AB, Gothenburg (SE)

( * ) Notice: Subject to any disclaimer, the term of this patent is extended or adjusted under 35 U.S.C. 154(b) by 125 days.

(21) Appl. No.: 15/771,632

(22) PCT Filed: Oct. 28, 2016

(86) PCT No.: PCT/EP2016/076064
§ 371 (c)(1),
(2) Date: Apr. 27, 2018

(87) PCT Pub. No.: WO2017/072296
PCT Pub. Date: May 4, 2017

(65) Prior Publication Data
US 2019/0382716 A1    Dec. 19, 2019

(30) Foreign Application Priority Data
Oct. 28, 2015   (GB) .................................. 1519087.9

(51) Int. Cl.
*C12N 1/36*    (2006.01)
*C12N 1/20*    (2006.01)
*C12R 1/01*    (2006.01)

(52) U.S. Cl.
CPC .................. *C12N 1/36* (2013.01); *C12N 1/20* (2013.01); *C12R 1/01* (2013.01)

(58) Field of Classification Search
CPC ................ C12N 1/20; C12N 1/36; C12R 1/01
See application file for complete search history.

(56) References Cited

U.S. PATENT DOCUMENTS

2015/0044172 A1*   2/2015   Bicalho .................. A23K 50/60
424/93.3

FOREIGN PATENT DOCUMENTS

WO    2009/120806    10/2009

OTHER PUBLICATIONS

Written Opinion and International Search Report corresponding to International Application No. PCT/EP2016/076064, dated Jan. 3, 2017, 14 pages.
Li, M. et al, "Enhanced biosynthesis of O-desmethylangolensin from daidzein by a novel oxygen-tolerant cock intestinal bacterium in the presence of atmospheric oxygen", Journal of Applied Microbiology, 118(3):619-628 (2015)(abstract).
Jasso-Chávez, Ricardo et al, "Air-Adapted Methanosarcina acetivorans Shows High Methane Production and Develops Resistance against Oxygen Stress", PLOS One, 10(2) 21 pages (2015).
Khan, M. Tanweer et al, "The gut anaerobe *Faecalibacterium prausnitzii* uses an extracellular electron shuttle to grow at oxic-anoxic interphases", The ISME Journal: Multidisciplinary Journal of Microbial Ecology, 6(8):1578-1585 (2012).
Khan, M. Tanweer et al, "Antioxidants Keep the Potentially Probiotic but Highly Oxygen-Sensitive Human Gut Bacterium *Faecalibacterium prausnitzii* Alive at Ambient Air", PLOS One, 9(5), 7 pages (2014).

* cited by examiner

*Primary Examiner* — Ruth A Davis
(74) *Attorney, Agent, or Firm* — Myers Bigel, P.A.

(57) ABSTRACT

The present invention relates generally to growth of bacteria. More specifically the invention relates to a method for oxidative environment adaptation of anaerobic microorganisms and their use in developing new probiotics. In particular, the present invention provides a method for adaptation of anaerobic microorganisms and selection of more oxygen tolerant anaerobic microorganisms, said method comprising the steps of culturing said microorganisms with a stepwise dual induction of oxidative stress via applied voltage and oxygen diffusion, and a stepwise change of anti-oxidant/oxidized counterpart concentration ratio to adjust the redox state. New strains are also provided.

11 Claims, 12 Drawing Sheets

METHOD FOR ADAPTATION

STATEMENT OF PRIORITY

This application is a 35 U.S.C. § 371 national phase application of International Application Serial No. PCT/EP2016/076064, filed Oct. 28, 2016, which claims the benefit, under 35 U.S.C. § 119 (a) of Great Britain Patent Application No. 1519087.9, filed Oct. 28, 2015, the entire contents of each of which are incorporated by reference herein.

FIELD OF THE INVENTION

The present invention relates generally to growth of bacteria. More specifically the invention relates to a method for oxidative environment adaptation of anaerobic microorganisms and their use in developing new probiotics. New (adapted) strains obtained by the methods of the invention are also provided.

BACKGROUND OF THE INVENTION

The adult gut microbiota consists of up to 100 trillion microorganisms, equivalent to ten times our total number of somatic and germ cells. The collective genomes of our gut microbes (microbiome) may contain more than 150 times more genes than our own genome and endow us with physiologic capacities we have not had to evolve on our own. These communities, however, remain largely unstudied, leaving almost entirely unknown their influence upon human development, physiology, immunity, nutrition and health. The microbial community has an immense capacity to affect host biology and is fundamental for the development of our immune system, the ability to process otherwise indigestible dietary polysaccharides, in addition to be a source for vitamin and hoinione production etc. Microbial communities in the large intestine have vital roles in the regulation of gut health and pathogenesis of several diseases.

Traditional microbiology has focused on the study of individual species as isolated units. However many, if not most, have never been successfully isolated as viable specimens for analysis, presumably because their growth is dependent upon a specific microenvironment that has not been reproduced experimentally. Advances in DNA sequencing technologies have created a new field of research, called metagenomics, allowing comprehensive examination of microbial communities, even those comprised of uncultivable organisms. Instead of examining the genome of an individual bacterial strain that has been grown in a laboratory, the metagenomic approach allows analysis of genetic material derived from complete microbial communities harvested from natural environments.

The human gut microbiome serves as a resource of beneficial microbes; potential probiotics. Despite both preventing and promoting roles of gut microbiota in diseases such as inflammatory bowel disease, cardiovascular disease, diabetes and autism spectrum disorder, no treatment available contains novel probiotics or the so called next generation probiotics as indicated by several metagenomics studies. Even if successfully isolated, many microbes isolated from gut, requires strict anaerobic conditions for growth and cannot survive more than a couple of minutes when exposed to ambient air. This makes it challenging to develop stable and robust probiotic formulations. There is a need therefore for more oxygen tolerant anaerobic microorganisms and the present invention provides a method for adaptation of anaerobic microorganisms, together with new strains of microorganisms that have been obtained using such methods.

SUMMARY OF THE INVENTION

The present invention provides a method for oxidative environment adaptation of anaerobic microorganisms, thus enabling such organisms to be relatively more oxygen tolerant when exposed to ambient air. This has the further advantage of enabling improved culturing and storage of the microorganisms, e.g. longer term storage.

Provided herein is a simulated human intestinal redox model (SHIRM) wherein a stepwise dual induction of oxidative stress, via applied voltage and oxygen diffusion, and a stepwise change of anti-oxidant/oxidized counterpart concentration ratio in order to adjust the redox state take place.

Oxygen is lethal for anaerobic microorganisms, so the dissolved oxygen (oxygen concentration), used for oxidative stress, will be increased but maintained at sub-lethal concentration, while anti-oxidant/oxidized counterpart couple is used to adjust redox state of environment. Oxidative stress is also induced via applied voltage. Oxidative stress increases the bacterial tolerance to oxidative environment and makes it possible to keep the microorganism alive at ambient air for relatively longer periods of time.

Appropriate sub-lethal oxygen concentrations (concentrations that do not result in the killing of all the bacteria present, or in other words concentrations in which some but not all of the bacteria are killed) can be readily determined, for example such that at least some (but generally not all) bacteria can survive and can then be selected to be taken to the next step in the methods. The surviving bacteria are then grown again, for example with an increase in oxidative stress (for example by increasing the dissolved oxygen concentration) such that again at least some (but generally not all) bacteria can survive and can then be selected to be taken to the next step in the method. This step of increasing oxidative stress can then be repeated again as many times as necessary or desired in order to achieve more oxygen tolerant microorganisms.

The present invention provides a method for adaptation of anaerobic microorganisms and selection of more oxygen tolerant anaerobic microorganisms, said method comprising the steps of culturing said microorganisms with a stepwise dual induction of oxidative stress via applied voltage and oxygen diffusion, and a stepwise change of redox state, wherein preferably the stepwise change of redox state takes place using a step-wise change of anti-oxidant/oxidized counterpart concentration ratio to adjust the redox state.

The present invention provides a method for adaptation (or training) of anaerobic microorganisms and selection of the more oxygen tolerant (e.g. relatively more oxygen tolerant) anaerobic microorganisms, wherein the microorganisms are cultured with a combination of a stepwise dual induction of oxidative stress, via applied voltage and oxygen diffusion, and a stepwise change of anti-oxidant/oxidized counterpart concentration ratio to adjust the redox state.

The present invention further provides a method for enhanced production of anaerobic microorganisms, wherein the microorganisms are cultured with a combination of constant oxidizing potential/applied voltage, oxygen diffusion, and anti-oxidant/oxidized counterpart concentration ratio, thus enabling a selective pressure and resulting in a high yield of certain strains of microorganisms. Said culture is in an optimal setting, or in other words, the combination of constant oxidizing potential/applied voltage, oxygen diffusion, and anti-oxidant/oxidized counterpart concentration ratio have been optimized for production of the anaerobic microorganisms.

DESCRIPTION OF FIGURES

FIG. 4a

Custom made 3 chambered Simulated Human Intestinal Redox Model (SHIRM).

FIG. 4b

Schematic presentation of electron flow from bacterial cells towards electron acceptors in SHIRM. Redox potentials (Reducing potential and Oxidising potential) measured in ($E_o'$) Volts.

FIG. 4c

SHIRM schematic presentation of intermediates involved in electron transfer from bacterial cell to the electron acceptors including redox potentials.

FIG. 5

Basic work flow of SHIRM operation.

FIG. 6

Representation of SHIRM anode chamber coupled to small bed volume ca 100 ml oxygen feeder.

FIG. 7

Air breathing SHIRM: direct oxygen diffusion from air into the anode chamber via side arm.

FIG. 8

Work flow of SHIRM operation, 10 steps

FIG. 9

Selection of adapted strains

FIG. 10

Strategy for exploring oxygen tolerance profiles of adapted strains.

DETAILED DESCRIPTION OF THE INVENTION AND PREFERRED EMBODIMENTS THEREOF

Definitions

"Adaptation" is a dynamic evolutionary process, e.g. a result of natural selections whereby an organism becomes better able to live in its habitat or habitats. The process of adaptation (or training) of microorganisms can also advantageously be carried out in a non-native/artificial/in vitro environment such as in the methods of the present invention.

"Antioxidant" is an agent that prevents the formation of reactive oxygen, nitrogen, hydroxyl and lipid species, by scavenging free radicals or by repairing or removing damaged molecules. Antioxidants often can act directly as reducing agents.

"Reducing agent" is a substance, element or compound that loses (or "donates") an electron to another agent in a redox chemical reaction. Since the reducing agent is losing electrons, it is said to have been oxidized.

"Oxidized counterparts" are chemicals causing removal of electron from another species. The oxidized counterpart is the oxidized form of the antioxidant.

"Redox mediators" or electron shuttles are compounds, which can undergo reversible redox reaction and facilitates the electron transfer/shuttle to and from bacteria.

"Applied voltage", "External voltage", "Oxidizing potential", "Applied electrical oxidizing potential", "Applied electrode potential", "Voltage" and "potential voltage" may be used interchangeably and refers to the voltage applied to the chambers in the bioreactor.

"Oxygen diffusion" is the movement of oxygen molecules from high to low concentration.

"Oxygen flux" is the amount of oxygen delivered per unit of time into the chamber, e.g. the anode chamber containing the microorganisms.

Figure 1:
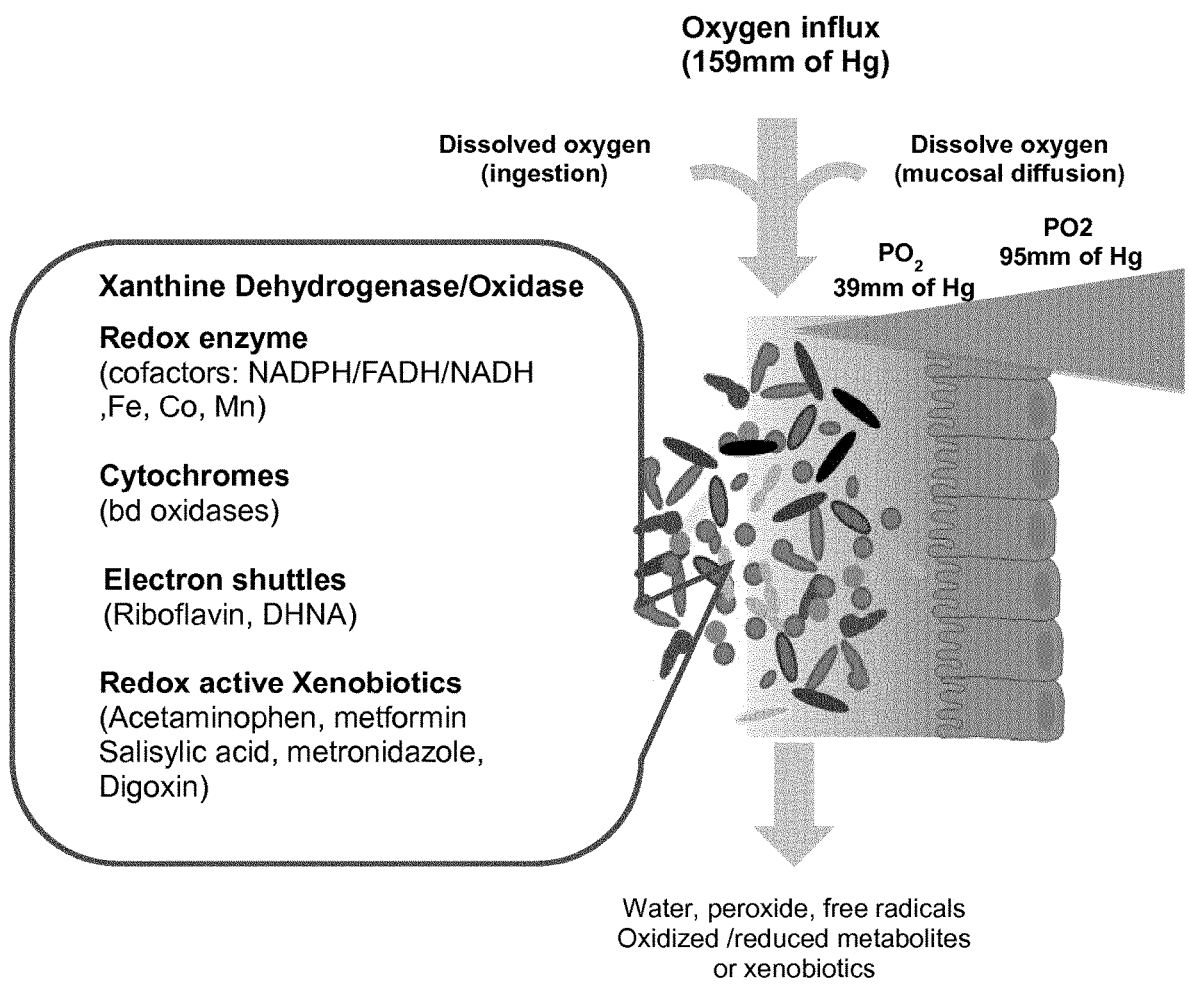
FIG. 1 shows the redox pool of human gut lumen. Despite the fact that there is continuous influx of oxygen via ingestion of food and diffusion from gut mucosa the net redox potential of the gut remains negative, ca −300 mV.
Figure 2:
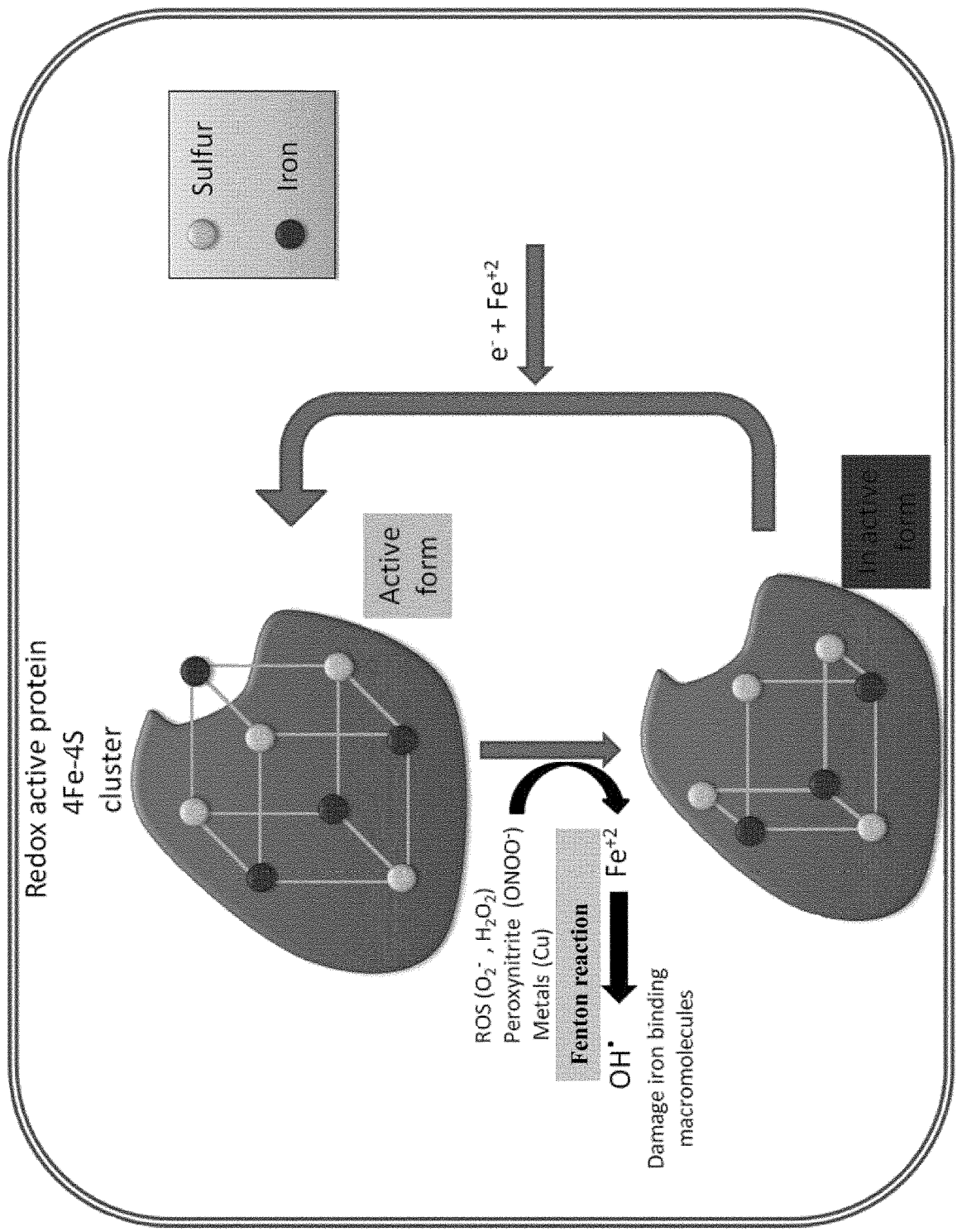
FIG. 2 shows the potential damage to the oxygen sensitive enzymes caused by oxidative stress and recovery mechanism.
Figure 3:
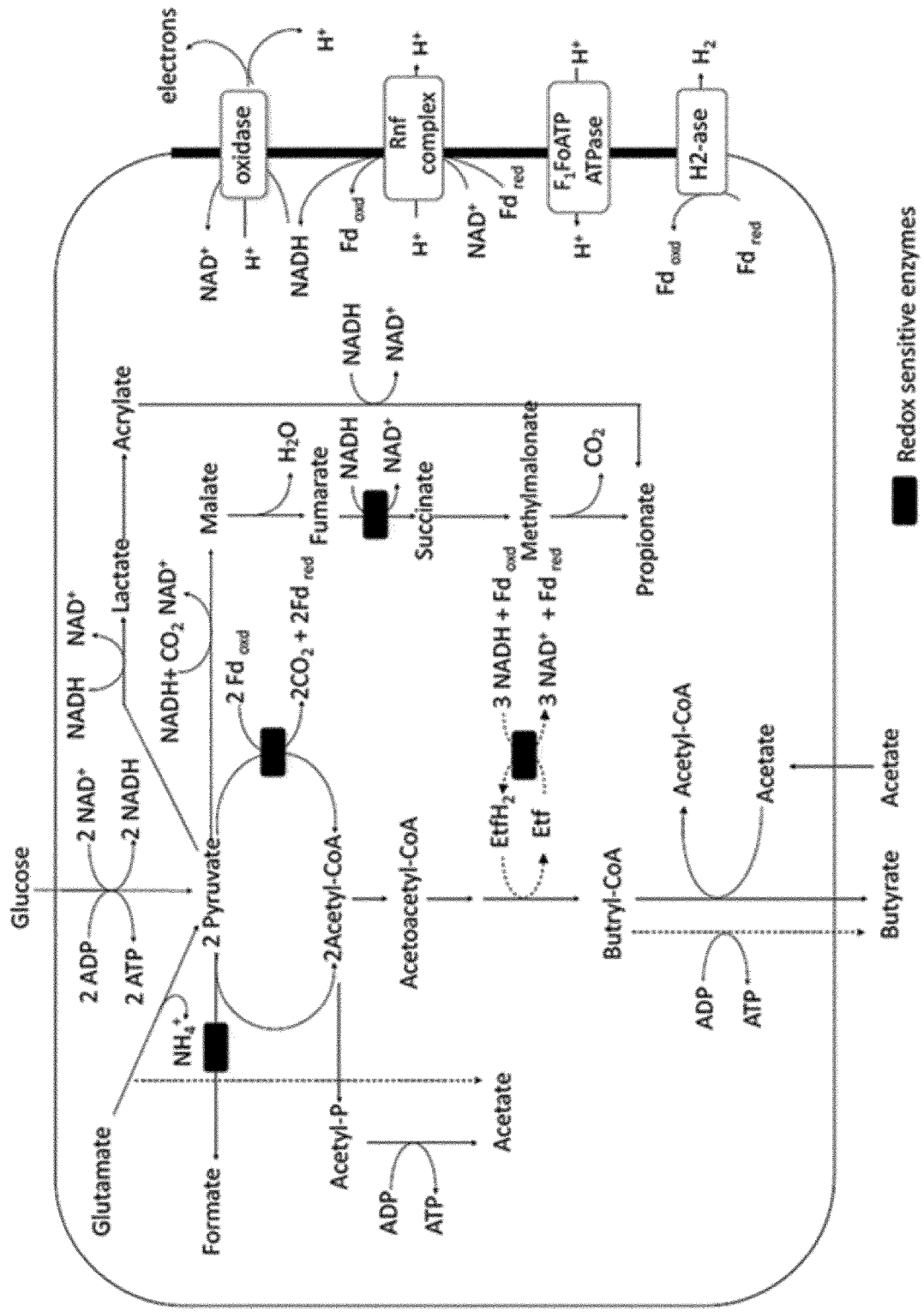
FIG. 3 shows the major fermentative pathway employed by gut microbiota in human gut.

Gut microbiota together with dietary redox active compounds and electron donors such as carbohydrates and proteins play a role in maintaining reducing environment in the gut. This means that the gut microbiota are adapted to cope with dissolved oxygen influxes in the gut lumen (FIG. 1). Dissolved oxygen in high concentrations can be lethal for a large number of gut microbes, and the reducing environment helps to recover from oxidative damage (FIG. 2). In more detail, FIG. 3 shows the major fermentative pathway employed by gut microbiota in the human gut. The electron disproportion during anaerobic growth is balanced by mixed acid fermentation and gas production. Some microbes respire electrons to extracellular electron acceptors such as nitrate, sulfate or insoluble metallic complex. Moreover, oxygen can act as indirect electron acceptor since some of the gut microbes can consume oxygen in small amounts. Redox active compounds such as gallate, rutin, resveratrol, caffeine and flavins are present in common diet, possibly oxidized in digestive tract can also act as electron acceptors (FIG. 1). The redox state of the gut may influence on the bioavailability of certain drugs or metabolites. Despite the fact that there is continuous influx of oxygen via ingestion of food and diffusion from gut mucosa the net redox potential of the gut remains negative, ca −300 mV. This oxygen deficient reducing environment favors the growth of strict anaerobic microbes in the gut lumen.

High sensitivity to oxygen is a hallmark of many gut microbes, which makes these microbes extremely hard to culture and store over long period of time. Another hurdle when isolating and culturing representatives of gut microbiota for developing new potential probiotics is the complexity of gut environment in terms of distinct niches and habitats. A probiotic formulation should be stable in ambient air for several months, but this is a challenge due to oxygen sensitivity of many gut microbes. Several gut microbes are cross feed from other microbes and may also require some growth factors from the host, which makes it challenging to stimulate these conditions in vitro.

*Faecalibacterium prausnitzii* is an example of a potential probiotic with anti-inflammatory properties in various metabolic diseases. It represents up to more than 5% of the bacteria in the human intestine, which makes it one of the most abundant bacterium in the intestinal microbiota. *F. prausnitzii* produces relatively high amounts of butyrate, which plays a major role in gut physiology and is a major metabolite in colonic lumen. Butyrate also stimulates cell proliferation and promotes mucus secretion from the colonic mucosa. *F. prausnitzii* is an extremely oxygen sensitive bacterium and only survives a couple of minutes when exposed to ambient air.

The inventors of the present invention have surprisingly found a new method for oxygen adaptation of anaerobic microorganisms and disclose herein a method for said oxygen adaptation, thus enabling such organisms to become relatively more oxygen tolerant and thereby stable and robust for storage and use as probiotic strains and in probiotic formulations or compositions for interventions in mammals. The new method would specifically allow development and use of *F. prausnitzii* as a probiotic strain with robust characteristics to tolerate industrial scale production and able to adapt to the human gut environment under gut disorders where oxidative stress is the major hallmark.

The present invention provides a method for adaptation of anaerobic microorganisms and selection of the relatively more oxygen tolerant anaerobic microorganisms, wherein the microorganisms are cultured in a combination of a stepwise dual induction of oxidative stress, via applied voltage and oxygen diffusion, and a stepwise change of anti-oxidant/oxidized counterpart concentration ratio to adjust the redox state. The methods of the invention are thus generally carried out in vitro.

The dual induction of oxidative stress increases the microorganisms' tolerance to oxidative environment, thus enabling the microorganism to be more, or relatively more, oxygen tolerant (e.g. when exposed to ambient air). Microorganisms which are more (or relatively more) oxygen tolerant (e.g. when exposed to ambient air) can conveniently refer to a comparison with the starting strain(s) (or parent strain(s)) used in the adaptation methods of the invention.

The increased oxygen tolerance makes it possible to keep the microorganisms alive in ambient air for relatively longer periods of time which is clearly advantageous.

The applied voltage or applied external voltage is generally applied to an anode, e.g. on a graphite, graphite felt or carbon felt or carbon fiber anode, via for example a potentiostat, and is increased stepwise. For the voltage to be applied to the microorganisms they are conveniently provided in an appropriate anode chamber or other vessel, e.g. a bioreactor, to which the voltage is applied. The cell circuit is completed, e.g. by connecting a cathode chamber to the anode chamber, e.g. via one side arm of the anode chamber, preferably separated by ion exchange membrane (e.g. a cation selective membrane or a proton exchange membrane). The applied voltage can be increased (preferably by way of a stepwise increase) to a maximum of 0.6V, more specifically of 0.6V vs Ag/AgCl.

Conveniently, the methods involve the use of oxygen diffusion, for example by the application of an oxygen flux to the microorganisms. Oxygen flux (e.g. oxygen flux through the anode chamber) may be maintained by purging an oxygen feeder with pure oxygen gas or air in order that the desired dissolved oxygen concentrations (in particular the desired dissolved oxygen concentrations in contact with the microorganisms) will be achieved. Dissolved oxygen will diffuse through the oxygen feeder to the anode chamber thereby creating the oxygen diffusion (or oxygen flux) of the described methods. Oxygen flux (or diffusion) can for example be controlled by any appropriate means, for example by connecting an oxygen feeder or other oxygen source to the anode chamber, e.g. another side arm of the anode chamber, separated via for example a variable septum (e.g. a variable membrane such as a semipermeable membrane) having different oxygen diffusion constants. Additionally or alternatively the oxygen flux may be controlled by changing the bed volume of the oxygen feeder. For example 100 ml and 250 ml oxygen feeders are shown in the Figures (see FIGS. 6 and 4a). The oxygen feeder can also be removed to allow direct diffusion of oxygen into the anode chamber as shown for example in FIG. 7. A membrane, e.g. a septum membrane, between the anode chamber and oxygen feeder (or oxygen source) can be further coated with mucin agar to allow better controlled diffusion of oxygen from oxygen feeder to anode chamber. Additionally, reducing agents or antioxidants present in the medium will scavenge dissolved oxygen and thus impact on the oxygen diffusion kinetics and hence oxygen flux. For example, in the methods of the present invention, antioxidants (in particular the amount or level of antioxidants) present in the microorganism culture medium can be used to scavenge oxygen and thereby can be used as a means to control the levels or amounts or concentration of oxygen (dissolved oxygen) present in the microorganism culture. For example, a low (or lower) level of antioxidant in the microorganism culture will generally mean that more oxygen is available (or there is more oxidative stress) whereas a high (or higher) level of antioxidant will generally mean that less oxygen (or a low level of oxygen) is available (or there is less oxidative stress).

Any of these methods for control of oxygen diffusion or flux, or a combination thereof, can readily be used to achieve the desired amount or concentration of dissolved oxygen in the microorganism culture medium and hence achieve the stepwise change (preferably stepwise increase) in oxygen diffusion, oxygen flux or dissolved oxygen concentration (or amount or level of dissolved oxygen) used to induce the oxidative stress in the methods of the present invention.

Thus, in the methods of the invention, the starting conditions are preferably low (or zero) oxygen flux (or oxygen diffusion or oxygen concentration) and the methods comprise a stepwise increase in oxygen flux (or oxygen diffusion or oxygen concentration), for example up to a high oxygen flux (or oxygen diffusion or oxygen concentration). Zero oxygen flux (or oxygen diffusion or oxygen concentration) refers to 0 moles of oxygen present in the microorganism culture medium (e.g. in the anodic chamber). An exemplary low oxygen flux (or oxygen diffusion or oxygen concentration) refers to about 10 µM of dissolved oxygen present in the microorganism culture medium (e.g. in the anodic chamber), which for example diffuses into the microorganism culture medium/anodic chamber in an hour (per hour). An exemplary high oxygen flux (or oxygen diffusion or oxygen concentration) refers to about 50 µM to about 250 µM of dissolved oxygen present in the microorganism culture medium (e.g. in the anodic chamber), which for example diffuses into the microorganism culture medium/anodic chamber in an hour (per hour).

The actual oxidative stress generated by the oxygen flux (or oxygen diffusion or oxygen concentration) is also dependent on the presence of antioxidants in the growth medium. For example, if you have high antioxidants, a high oxygen flux will produce less oxidative stress. If you have very low antioxidants in the medium a small oxygen flux can generate high oxidative stress. Again control of these conditions is well within the capability of the skilled person in order to achieve the stepwise induction of oxidative stress.

To control the starting concentration of dissolved oxygen (e.g. to reduce the starting concentration of oxygen to low (or zero) levels), the growth medium can be degassed of oxygen, e.g. by purging with oxygen free nitrogen.

Anti-oxidant is included in the culture medium in order to protect the microorganisms from lethal concentrations of oxygen and to simulate gut redox environment. For example the antioxidant may be cysteine, glutathione, ascorbic acid, dithiothreitol or gallic acid. The antioxidant, for example cysteine or any other suitable antioxidant, will be used in order to affect or adjust the redox potential or redox state. Many bacteria require cysteine as a source of sulfur. When cysteine, as in some of the methods of this invention, is reduced this will lead to a decreased total sulfur pool of the growth medium. To compensate that decrease, the oxidized counterpart, for example cystine (in the case of cysteine) is added. Other oxidized counterparts (e.g. for the antioxidants listed above) may be glutathione-oxidized state, dehydroascorbate, oxidized dithiothreitol or oxidized gallic acid, as appropriate. Additionally, suitable redox mediators can also be included in the culture media.

The stepwise change of redox state, e.g. the stepwise change of anti-oxidant/oxidized counterpart concentration ratio, is performed to adjust the redox state of the growth environment. The redox potential may be calculated according to the Nernst equation (a). This may be used for any suitable antioxidant and its oxidized counterpart.

$$E_h = E_o + \frac{RT}{nF} \ln\left(\frac{[\text{Oxidized counterpart}]}{[\text{Reducing agent}/\text{Antioxidant}]^2}\right) \quad (a)$$

where:

$E_h$=redox potential=V $E_o$=Standard redox potential of (Reducing agent/Antioxidant)/Oxidized Counterpart couple
R=General gas constant=8.31451 J K$^{-1}$ mol$^{-1}$
F=Faradays constant=96.485 C/mol
T=Absolute temperature (K)
n=number of electrons involved The redox potentials of any anti-oxidant/oxidized counterpart concentration ratio can thus readily be calculated by a person skilled in the art. By way of example, the redox potential ($E_h$) values calculated for various concentrations of cysteine/cystine redox couple are presented in Table 1.
$E_o$ for Cystine/Cysteine couple=0.25V at pH 7.4 and n=2.
If using cysteine/cystine as antioxidant/oxidized counterpart couple the preferred starting concentration of cysteine could be calculated based on reaction formula (b).

4R—SH+O$_2$→2R—SS—R+H$_2$O  (b)

According to the equation (b), 4 moles of cysteine (R—SH) react with one mole of oxygen to produce 2 moles of cystine (R—SS—R).

The dissolved oxygen concentration in water at 25° C. is around 200 µM, and when the growth medium is not purged with nitrogen prior to the experiment around 800 µM of cysteine will react with 200 µM of oxygen generating 400 µM of cystine. Thus for growth medium having 8 mM of cysteine an initial redox potential of around −223 mV will be observed. However, the complete degassing of oxygen in growth medium with oxygen free nitrogen provides a redox potential of around −283 mV, close to the gut luminal redox potential (around −300 mV). Thus, where cysteine/cystine is used as a couple, the preferred starting concentration of cysteine (or other anti-oxidant counterpart couple) is 8 mM. This is an example of a high concentration of antioxidant where cysteine/cystine is used as a couple, however it will be appreciated that equivalent high concentrations of antioxidants can readily be calculated for other couples. In addition, the preferred starting concentration of cystine (or other oxidized counterpart couple) is 0 mM or an otherwise low concentration in order to achieve the desired starting redox potential. It is also preferred that the growth medium used has been completely degassed of oxygen (or that oxygen has been completely removed from the growth medium). In other words, preferred conditions are chosen to get as close to the gut luminal redox potential of −300 mV as possible at the start of the method. When carrying out the methods it is preferred that a stepwise reduction in the concentration of antioxidant combined with a stepwise increase in the concentration of oxidized counterpart takes place to result in an overall stepwise increase in the redox potential. Conveniently for cysteine/cystine (or other antioxidant/oxidized counterpart couple) this can be a stepwise reduction of 1 mM in the concentration of cysteine and an increase of 1 mM in the concentration of cystine. However, different stepwise increases/decreases can also be used providing that a stepwise change in redox state takes place.

This reasoning may be adapted to any suitable antioxidant/oxidized counterpart couple. When decreasing the antioxidant concentration, this is balanced with equivalent amount of corresponding oxidized counterpart.

The method can conveniently be carried out in a suitable bioreactor and generally involves several steps of reinoculations of bacterial culture (e.g. into new culture media). In some preferred embodiments of the invention, each step of the stepwise change or induction as described herein, e.g. a stepwise dual induction of oxidative stress via applied voltage and oxygen diffusion, and a stepwise change of anti-oxidant/oxidized counterpart concentration ratio to adjust the redox state, e.g. each step of the stepwise reduction in the concentration of antioxidant combined with a stepwise increase in the concentration of the oxidized counterpart, a stepwise increase in applied voltage and a stepwise increase in oxygen flux (or oxygen diffusion or oxygen concentration), can involve a reinoculation. Reinoculation can also be referred to herein as a subculture step or a culture step.

At first, a single colony of bacteria can be inoculated into an appropriate culture media as known in the art and allowed to grow until the culture reaches stationary phase. Starting conditions can be one or more, or all, of low oxygen flux (or oxygen diffusion or oxygen concentration), preferably zero oxygen flux (or oxygen diffusion or oxygen concentration), low applied voltage, preferably 0.1 V, more specifically 0.1 V vs Ag/AgCl, high concentration of anti-oxidant (see Nernst equation calculations above), low concentration, or zero concentration, of oxidized counterpart (see Nernst equation calculations above). For the following reinoculations a stepwise decrease of anti-oxidant concentration, increase of oxidized counterpart, increased applied voltage, and increased oxygen flux (or oxygen diffusion or oxygen concentration) can be carried out.

When the growth of the microorganisms is significantly decreased, the conditions can be kept constant at the optimized (or final) conditions reached, which can be exemplified with 3 mM cysteine, 5 mM cysteine, 0.6 V vs Ag/AgCl and 0.2 nmolesml$^{-1}$min$^{-1}$respectively (see FIGS. 5 and 8), in order to let the strain adapt. In other words, once the stepwise changes result in the growth of the microorganisms being significantly decreased, then these stepwise changes are stopped and the microorganisms are cultured for one or more steps using constant conditions (or optimized or final conditions) corresponding to those conditions reached at the end of the stepwise changes. These constant steps allow the strains to adapt. After repeated inoculations at constant conditions, once the strain has adapted, in some embodiments inoculations can be continued with one or more (or preferably all) of a further stepwise decrease of anti-oxidant concentration, increase of oxidized counterpart, increased applied voltage, and increased oxygen flux (or oxygen diffusion or oxygen concentration), (see FIG. 5).

All subcultures obtained from each step of the method can be analyzed at once in order to select the best adapted strain or a subculture can be analyzed directly after retrieval to decide if inoculations should be continued or not. If the subculture has not adapted, then it will be appropriate to continue with inoculations, otherwise, if the strain has adapted, then that strain can be selected and the method can be stopped (see e.g. FIG. 8). For example, the sub-cultures obtained can be analysed for oxygen tolerance and if they show the desired level of oxygen tolerance, e.g. an increased (preferably significantly increased) level of oxygen tolerance compared to a relevant control strain (e.g. the starting or parent strains) or a sufficient level of stability (e.g. storage time) when exposed to oxygen (e.g. in ambient air) then the strain has adapted and can be selected. A convenient measure of oxygen tolerance can be obtained by assessing growth of the microorganisms in aerobic conditions (e.g. with exposure to ambient air). For example, a measure of the number of colony forming units (CFUs) can be made when the strains are exposed to oxygen, e.g. in the form of a measure of CFU/ml. Exemplary adapted (oxygen tolerant) strains will have at least $1\times10^2$ or $1\times10^3$ CFU/ml, preferably at least $1\times10^4$ or $1\times10^5$ CFU/ml, when exposed to oxygen, e.g. ambient air. An appropriate method is described in the Examples (see e.g. Table 3). If the strain has not adapted then inoculations can be continued.

Thus, in preferred embodiments of the invention, the starting conditions are selected from one or more, or all, of: 8 mM cysteine (or equivalent concentration of an alternative antioxidant), 0 mM cystine (or alternative oxidised counterpart), an applied voltage of 0.1V, and zero or low oxygen flux. In such embodiments, the stepwise changes can be continued until one or more, or all, of: a minimum cysteine concentration of 3 mM (or equivalent concentration of an alternative antioxidant), a maximum cystine concentration of 5 mM (or equivalent concentration of an alternative oxidised counterpart), a maximum applied voltage of 0.6 V, and a high oxygen flux.

Thus, in preferred methods of the invention, the applied voltage does not exceed 0.6 V, and/or the cysteine concentration is no lower than 3 mM, and/or the cystine concentration is no higher than 5 mM, and/or the dissolved oxygen concentration in the culture medium is maintained at a sub-lethal concentration.

Figure 8:
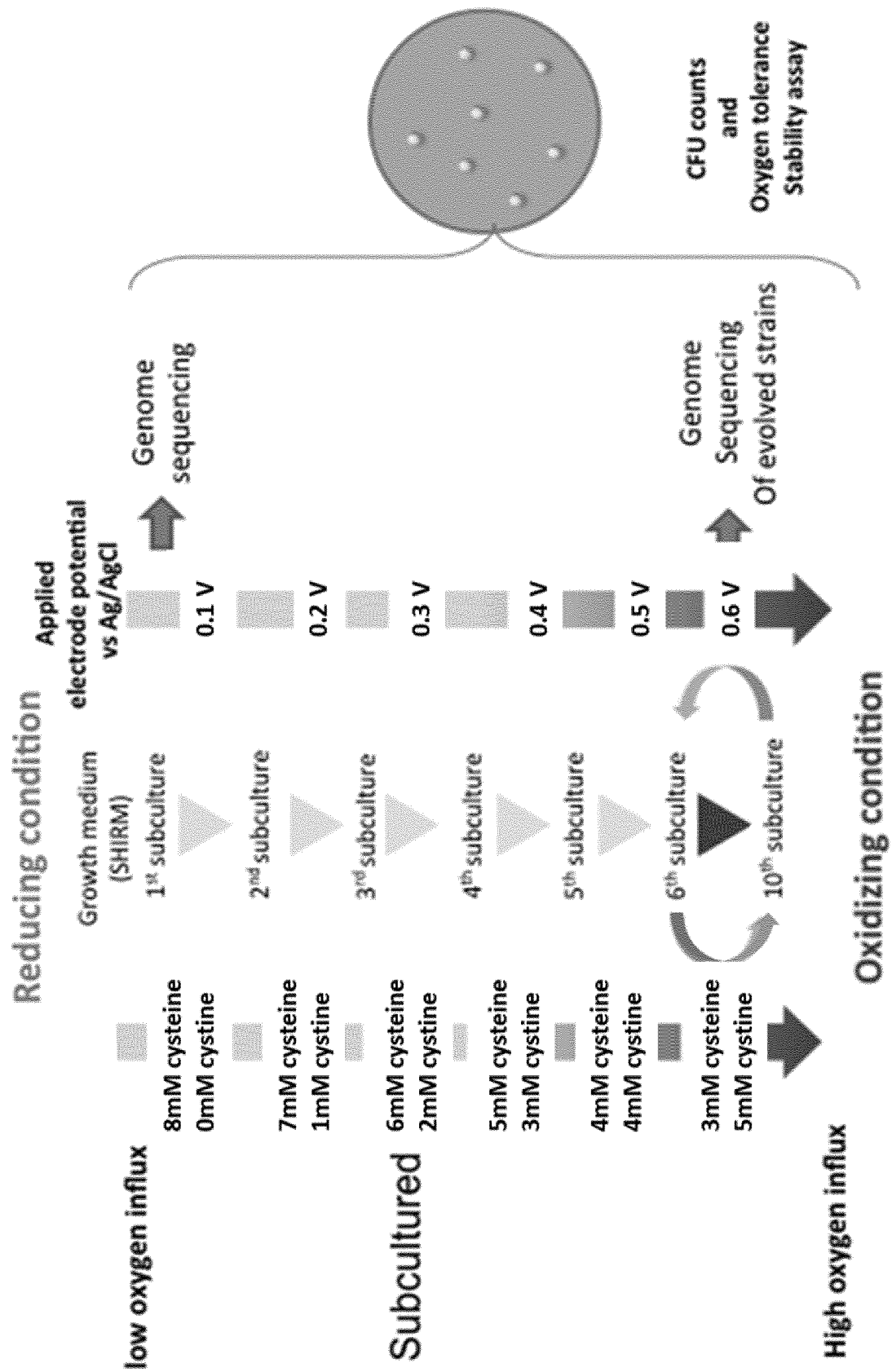

As will be clear from the discussion above, in some embodiments of the invention, once the stepwise changes have been completed, the method comprises one or more further steps of culturing (subculturing) said microorganisms under the final (optimized or constant) conditions of applied voltage, oxygen diffusion (oxygen flux or oxygen concentration) and anti-oxidant/oxidized counterpart concentration ratio reached after the stepwise changes (see for example FIG. 8).

Figure 5:
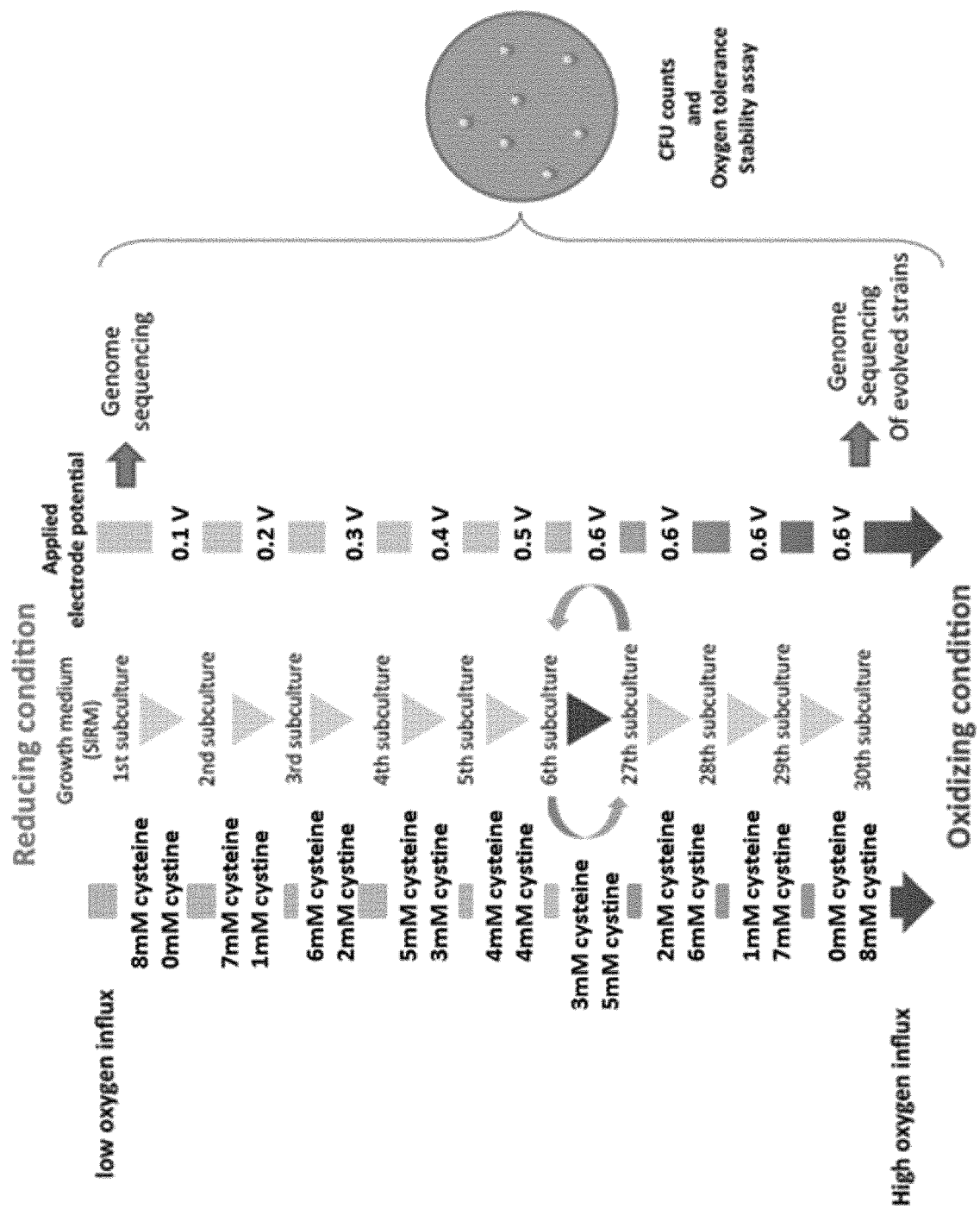

In other embodiments, the method further comprises subsequent steps in which further stepwise changes are carried out (see for example FIG. 5).

Determining the number of steps of stepwise changes to be carried out can be determined by a skilled person in the art by monitoring the behaviour of the microorganisms or screening the microorganisms (e.g. as described elsewhere herein), whilst they are undergoing adaptation. For example, preferred embodiments of the present methods may involve up to 5 or 6 steps of stepwise changes, e.g. 3, 4, 5 or 6 steps of stepwise changes, or at least 5 steps of stepwise changes, e.g. up to 10 steps of stepwise changes, e.g. 7, 8, 9 or 10 steps.

Determining the total number of steps, e.g. culturing steps (including steps of stepwise changes and steps to be carried out under constant or optimized conditions) in order to achieve adaptation of anaerobic microorganisms and selection of more oxygen tolerant anaerobic microorganisms, can be determined by a skilled person in the art by monitoring the behaviour of the microorganisms or screening the microorganisms (e.g. as described elsewhere herein), whilst they are undergoing adaptation. For example, preferred embodiments of the present methods may involve up to 6, 7, 8, 9, 10 or 12 steps, or up to 15, 20, 25, 30 or 35 steps.

In methods which involve culturing steps to be carried out under constant or optimized conditions, determining the number of steps, e.g. culturing steps to carry out, can be determined by a skilled person in the art by monitoring the behaviour of the microorganisms or screening the microorganisms (e.g. as described elsewhere herein), whilst they are undergoing adaptation. For example, preferred embodiments of the present methods may involve up to 3, 4, 5, 6, 7, 8, 9, 10 or 12 steps, or up to 15, 20, 25, 30 or 35 steps carried out under constant or optimized conditions.

In some embodiments adaptation of anaerobic microorganisms and selection of more oxygen tolerant anaerobic microorganisms can be achieved at the end of these steps carried out under constant or optimized conditions (or indeed sometimes at the end of the steps of stepwise changes). Thus, the skilled person in the art can readily determine the number of such steps to carry out, e.g. by monitoring for when significant or sufficient or maximum adaptation (oxygen tolerance) has occurred.

The method can also be used for production of an adapted and selected strain (e.g. for the production or growth of a microorganism selected by the method). In such methods the culturing conditions are kept constant at an optimum setting, e.g. the optimized (or constant) conditions as established using the above described methods of the invention, e.g. 3 mM anti-oxidant, 5 mM oxidized counterpart, 0.6 V and 0.2nmolesml$^{-1}$min$^{-1}$. This results in a high yield of the selected bacterial strain.

Figure 4:
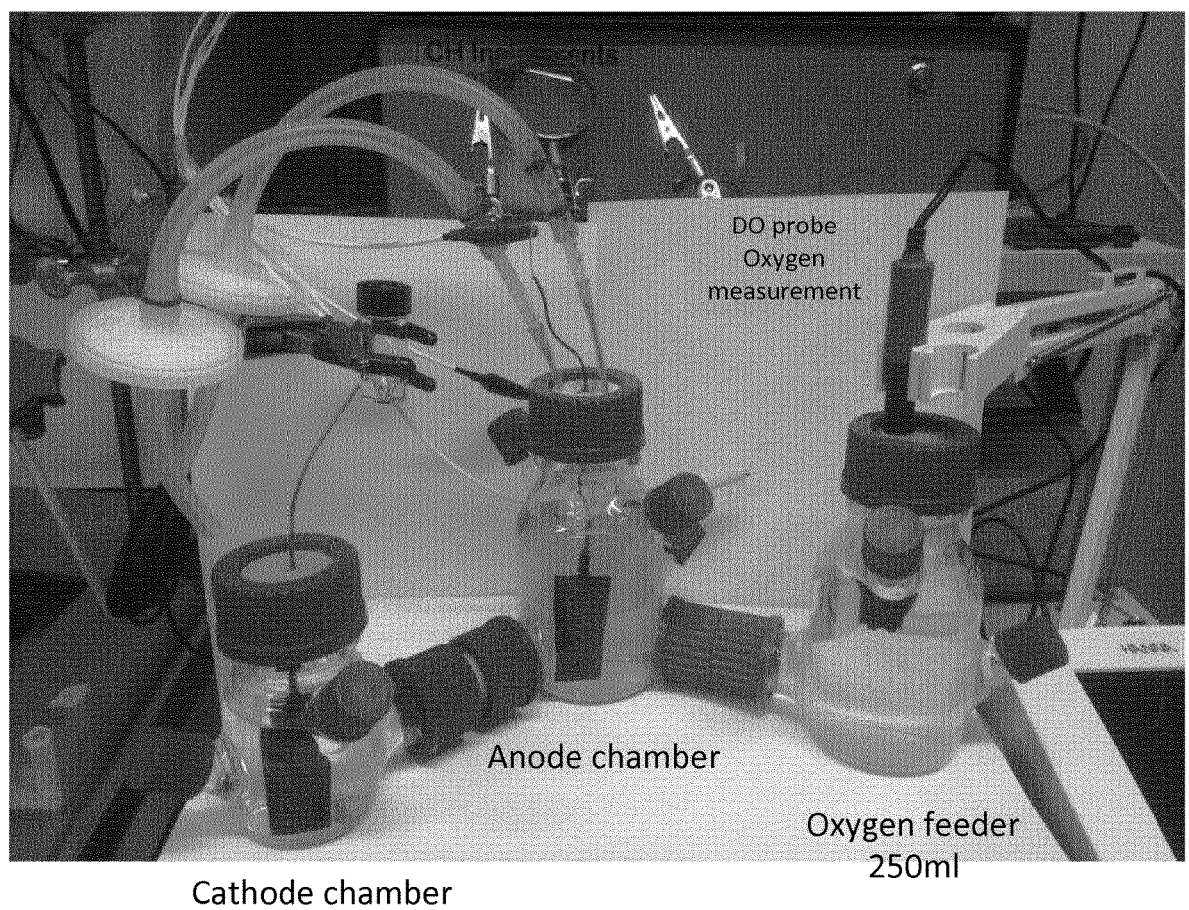
Figure 4:
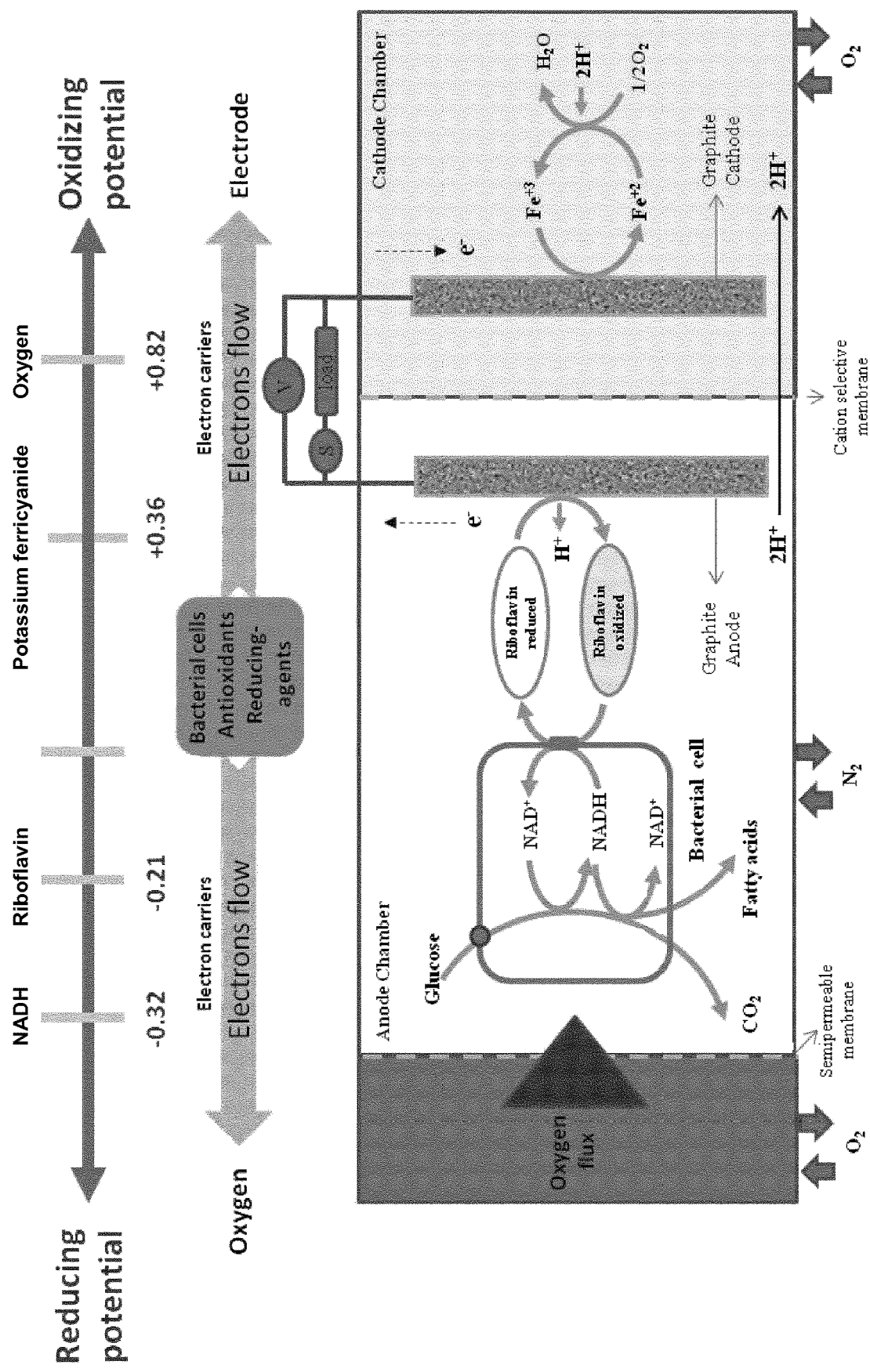
Figure 4:
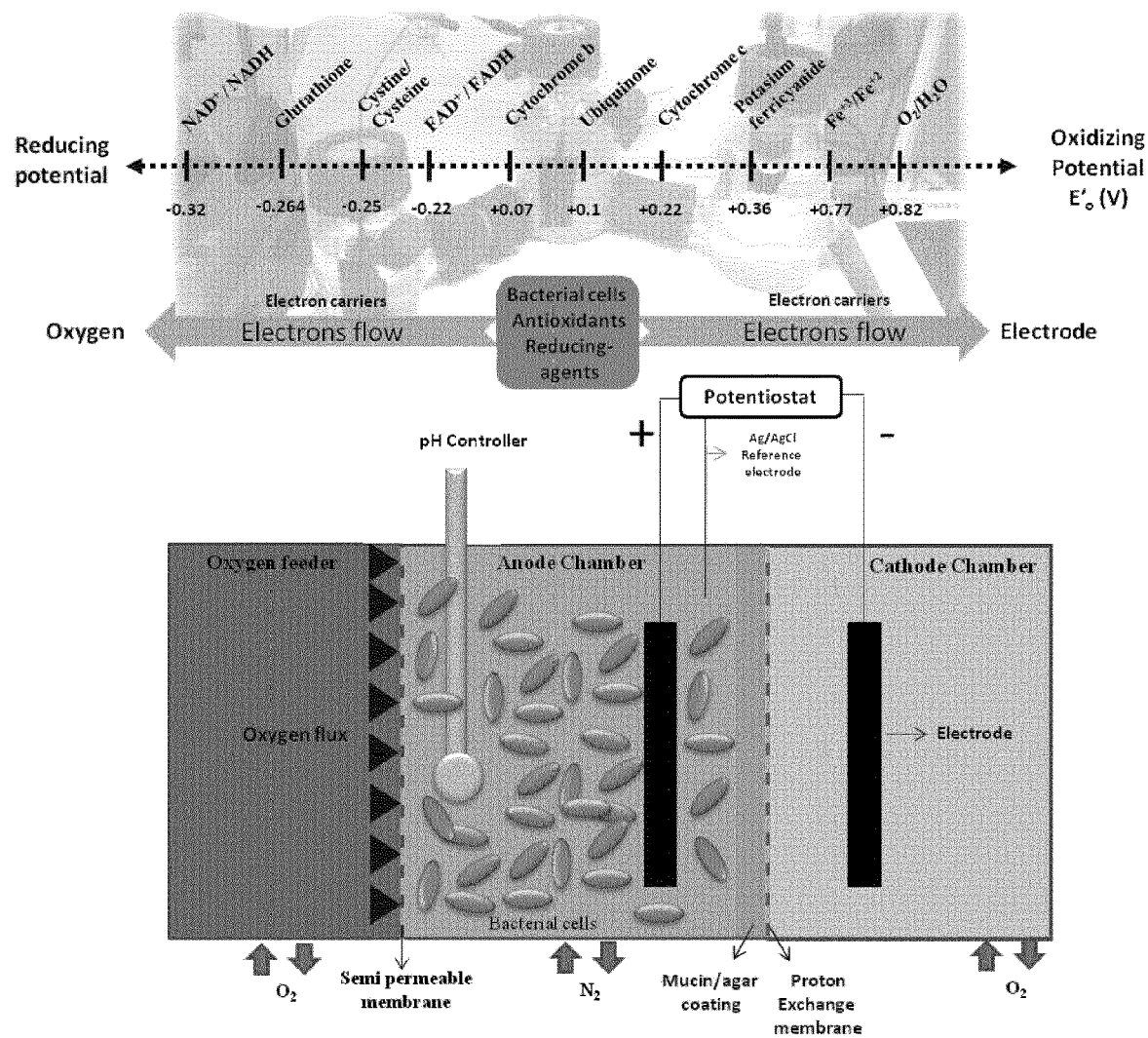

The method is conveniently carried out in a bioreactor called 'Simulated Human Intestinal Redox Model' (SHIRM), FIG. 4a, b and c. In SHIRM dual oxidative stress is applied via external voltage (applied voltage) and oxygen diffusion (oxygen flux) and the redox potential/redox state of the system is controlled by anti-oxidant/oxidized counterpart couple. Since oxygen is lethal for the cultured organisms, the dissolved oxygen will be increased but maintained at sub-lethal concentration, while a stepwise change of anti-oxidant/oxidized counterpart concentration ratio is used to adjust the redox state of the environment (see for example FIG. 5 or FIG. 8 which shows exemplary cysteine/cystine concentrations, which can be readily adapted to other anti-oxidant/oxidized counterpart couples). Oxidative stress via applied voltage and oxygen diffusion increases the bacterial tolerance to oxidative environment and the cells are repeatedly challenged to new oxidative conditions (e.g. FIG. 5 or FIG. 8). Adapted or evolved strains are screened for oxygen tolerance. Strains can also be screened for metabolic characteristics, such as fatty acid profile (e.g. butyrate production in the case of a butyrate producing bacteria such as *Faecalibacterium prausnitzii*) and assessment of growth kinetics, in order to select the best adapted strain. The adapted or evolved strains are thus adapted to be better tolerant (e.g. than the relevant starting or parent microorganisms) to an oxygen containing environment or to be better tolerant to stress conditions such as exposure to ambient air (oxidative stress) or to for example bile salts. Thus, where for example the strains are *Faecalibacterium prausnitzii*, strains are selected where metabolic characteristics such as butyrate production, or other fatty acid production, is maintained or improved, but the strains show an improved oxygen tolerance (e.g. compared to the relevant starting or parent *Faecalibacterium prausnitzii* strain).

In a preferred embodiment the present invention provides a method for adaptation of anaerobic microorganisms and selection of the relatively more oxygen tolerant anaerobic microorganisms, wherein the microorganisms are cultured in a combination of a stepwise dual induction of oxidative stress, via applied voltage and oxygen diffusion, and a stepwise change of anti-oxidant/oxidized counterpart concentration ratio to adjust the redox state.

In yet another preferred embodiment the method for oxygen adaptation of anaerobic microorganisms is carried out using a bioreactor called Simulated Human Intestinal Redox Model (SHIRM) and includes, but is not limited to, the following steps:

a) Inoculation of a single colony of bacteria in culture media (as known in the art) including suitable redox mediators and reducing agents to protect the bacterial cells from lethal concentrations of oxygen and to simulate gut redox environment.

b) When the culture reach late exponential phase, one part of the culture can be used for analysis and another part can be used for possible re-inoculation into the SHIRM reactor.

c) Inoculation of the culture in the SHIRM reactor containing the same culture media as used in the primary isolation and routine cultivation of the bacterial strain. The growth medium now called Shirm Bed Culture Medium (SBCM)

I. Reducing agent/anti-oxidant concentration, for example but not limited to cysteine, glutathione, ascorbic acid, dithiothreitol and gallic acid, is decreased and balanced with equivalent amount of a corresponding "oxidized counterpart", for example but not limited to cystine, glutathione-oxidized state, dehydroascorbate, oxidised dithiothreitol and oxidized gallic acid.

II. The applied electrical oxidizing potentials are maintained via external voltage, e.g. on graphite, graphite felt or carbon felt or carbon fiber anode via potentiostat. The cell circuit is completed, e.g. by connecting cathode chamber to one side arm of anode chamber separated by proton exchange membrane.

III. Oxygen flux is controlled by connecting oxygen feeder to other side arm of the anode chamber separated via variable septum having different oxygen diffusion constants. The instantaneous oxygen flux is measured, for example by Clark's type DO probe, see FIG. 4A.

IV. The oxygen flux is maintained by purging oxygen feeder with pure oxygen gas or air and desired dissolved oxygen concentrations are achieved following Henry's law of gas solubility. Dissolved oxygen then diffuses through the oxygen feeder to anode chamber.

V. Additionally the oxygen flux is controlled by changing the bed volume of oxygen feeder. The oxygen feeder can also be removed to allow direct diffusion of oxygen into the anode chamber.

VI. The septum membrane between anode chamber and oxygen feeder can be further coated with mucin agar to allow better controlled diffusion of oxygen from oxygen feeder to anode chamber.

VII. The SHIRM contains Shirm Bed Culture Media (SBCM), which is purged with oxygen free nitrogen to remove dissolved oxygen.

VIII. The SHIRM bioreactor is run until the culture reaches the stationary phase.

d) One part of the first subculture is used for inoculation in the SHIRM reactor.

e) Re-inoculation in the SHIRM reactor is initiated having stepwise decreased anti-oxidant concentration, increased oxidized counterpart concentration and increased applied voltage (maximum 0.6V). Less anti-oxidant will scavenge less oxygen therefore more oxygen will be available and cells experience more oxidative stress. Oxygen feeder further regulates the oxygen diffusion flux. This step is repeated until the growth is decreased.

f) Keeping all conditions constant, re-inoculations is repeated and the new subculture is analyzed for comparative metabolic characterization, growth kinetics, stability and tolerance. If the analysis is satisfying then this subculture is selected and if not step f) is repeated.

In such methods each subculture can be analysed before subsequent re-inoculation (or analysed after each step) and the method is stopped when the strain has adapted suitably to oxygen. This strain is then selected. In such methods up to about 30 subcultures, or up to about 10 subcultures (or other numbers of subcultures as described elsewhere herein), may be analysed before the method is stopped.

One or more of the above steps can be used, as appropriate, in any of the methods of the invention as described herein.

In another preferred embodiment, about 30 subcultures are retrieved (see for example FIG. 5) or about 10 subcultures are retrieved (see for example FIG. 8) or other numbers of subcultures are retrieved (as described elsewhere herein) and then all are analyzed in order to find best suitable strain. In this way it is not necessary to analyze the subcultures after each step but instead all analyzes can be performed at once, e.g. to assess which subculture is most adapted or tolerant to oxygen. The method for oxygen adaptation of anaerobic microorganisms is carried out using a bioreactor called Simulated Human Intestinal Redox Model (SHIRM) and includes, but is not limited to, the following steps:

a) Inoculation of a single colony of bacteria in routine culture media as known in the art including suitable redox mediators and reducing agents to protect the bacterial cells from lethal concentrations of oxygen and to simulated gut redox environment.

b) When the culture reach late exponential phase, one part of the culture is used for inoculation into the SHIRM reactor and another part saved for analysis.

c) Inoculation of the culture in the SHIRM reactor containing the same culture media as used in the primary isolation and routine cultivation of the bacterial strain. The growth medium now called Shirm Bed Culture Medium (SBCM)

I. Reducing agent/anti-oxidant concentration, for example but not limited to cysteine, glutathione, ascorbic acid, dithiothreitol and gallic acid, is decreased and balanced with equivalent amount of a corresponding "oxidized counterpart", for example but not limited to cystine, glutathione-oxidized state, dehydroascorbate, oxidised dithiothreitol and oxidized gallic acid.

II. The applied electrical oxidizing potentials are maintained via external voltage on graphite, graphite felt or carbon felt or carbon fiber anode via potentiostat. The cell circuit is completed by connecting cathode chamber to one side arm of anode chamber separated by proton exchange membrane.

III. Oxygen flux is controlled by connecting oxygen feeder to other side arm of the anode chamber separated via variable septum having different oxygen diffusion constants. The instantaneous oxygen flux is measured, for example by Clark's type DO probe, see FIG. 4A.

IV. The oxygen flux is maintained by purging oxygen feeder with pure oxygen gas or air and desired dissolved oxygen concentrations are achieved following Henry's law of gas solubility. Dissolved oxygen then diffuses through the oxygen feeder to anode chamber.

V. Additionally the oxygen flux is controlled by changing the bed volume of oxygen feeder. The oxygen feeder can also be removed to allow direct diffusion of oxygen into the anode chamber.

VI. The septum membrane between anode chamber and oxygen feeder can be further coated with mucin agar to allow better controlled diffusion of oxygen from oxygen feeder to anode chamber.

VII. The SHIRM contains SBCM, which is purged with oxygen free nitrogen to remove dissolved oxygen.

VIII. Then SBCM used for first inoculation, can be designated as SBCM X,Y/$V_Z$, where X refers to the anti-oxidant concentration (mM) and Y refers to the oxidized counterpart concentration (mM) and '$V_Z$' indicates the applied voltage vs Ag/AgCl (V). The SHIRM bioreactor is run until the culture reaches the stationary phase.

IX. The culture retrieved after first incubation can be designated as "Population P1".

d) Next inoculation in the SHIRM reactor is initiated having decreased anti-oxidant concentration, increased oxidized counterpart concentration and increased applied voltage. Less anti-oxidant will scavenge less oxygen therefore more oxygen will be available and cells experience more oxidative stress. Oxygen feeder further regulates the oxygen diffusion flux.

e) The reinoculations are continued until about $6^{th}$ subculture, see e.g. FIGS. 5 and 8 (when the combined effect of the antioxidants/redox mediators, oxygen flux and voltage significantly influence (decrease) the growth).

f) The applied voltage will generally not be increased beyond 0.6V vs AgAgCl because of overpotential. Higher potentials may cause rapid fouling of electrodes, and additionally lethal oxidations of microbial cytochromes for example cytochrome a3 possess a reduction potential of around +0.385V vs SHE.

g) Keeping all conditions constant, repeated inoculations was performed until about $27^{th}$ subcultures (see e.g. FIG. 5) or until about $10^{th}$ subculture (see e.g. FIG. 8), more precisely adequate number of subcultures (to increase the probability of adaptation) until the strain has adapted to the conditions, while at every subculture fresh medium was used.

h) After the $27^{th}$ subculture, the inoculations continued up to about $30^{th}$ subculture as shown in FIG. 5. Alternatively, after the $10^{th}$ subculture, the inoculations were stopped as shown in FIG. 8.

i) When all subcultures are retrieved they are analyzed for comparative metagenomics, metabolic characterization, growth kinetics, stability and oxidative stress tolerance in order to choose the best adapted strain.

One or more of the above steps can be used, as appropriate, in any of the methods of the invention as described herein.

In yet another embodiment, the method for oxygen adaptation of anaerobic microorganisms is carried out using a bioreactor called Simulated Human Intestinal Redox Model (SHIRM) and includes, but is not limited to, the following steps:

a) Inoculation of a single colony of bacteria in routine culture media, as known in the art. Cysteine is employed to simulate colonic redox potential of the growth medium and resazurin as used redox indicator.

b) When the culture reach late exponential phase, one part of the culture is used for inoculation into the SHIRM reactor and another part saved for analysis.

c) Inoculation of the culture in the SHIRM reactor containing the same culture media as used in the primary isolation and routine cultivation of the bacterial strain. The growth medium now called Shirm Bed Culture Medium (SBCM)

I. The reducing agent/anti-oxidant concentration, cysteine, is decreased and balanced with equivalent amount of a corresponding "oxidized counterpart", cystine.

II. The applied electrical oxidizing potentials are maintained via external voltage on graphite, graphite felt or carbon felt or carbon fiber anode via potentiostat. The cell circuit is completed by connecting cathode chamber to one side arm of anode chamber separated by proton exchange membrane.

III. Oxygen flux is controlled by connecting oxygen feeder to other side arm of the anode chamber separated via variable septum having different oxygen diffusion constants. The instantaneous oxygen flux is measured, for example by Clark's type DO probe, see FIG. 4A.

IV. The oxygen flux is maintained by purging oxygen feeder with pure oxygen gas or air and desired dissolved oxygen concentrations are achieved following Henry's law of gas solubility. Dissolved oxygen then diffuses through the oxygen feeder to anode chamber.

V. Additionally the oxygen flux is controlled by changing the bed volume of oxygen feeder. The oxygen feeder can also be removed to allow direct diffusion of oxygen into the anode chamber.

VI. The septum membrane between anode chamber and oxygen feeder can be further coated with mucin agar to allow better controlled diffusion of oxygen from oxygen feeder to anode chamber.

VII. The SHIRM contains SBCM, which is purged with oxygen free nitrogen to remove dissolved oxygen.

VIII. Then SBCM used for first inoculation, may be designated as SBCM 8.0/$V_{0.1}$ former indicates the cysteine concentration while later cystine concentration in mM and 'V' indicates the applied voltage vs Ag/AgCl. The SHIRM bioreactor runs until the culture reaches the stationary phase under an oxidizing potential of +100 mV.

IX. The culture retrieved after first incubation may be designated as "Population P1".

d) Next inoculation in the SHIRM reactor is initiated having decreased cysteine concentration, increased cystine concentration and increased applied voltage, see FIG. 5 and FIG. 8. Less anti-oxidant will scavenge less oxygen therefore more oxygen will be available and cells experience more oxidative stress. Oxygen feeder further regulates the oxygen diffusion flux.

e) The reinoculations are continued until 6$^{th}$ subculture. At this stage the anti-oxidant is reduced to 3 mM and the "oxidized counterpart" is increased to 5 mM while oxidizing potential is raised to 0.6V (vs AgAgCl). The potential voltage will not be increased beyond 0.6V vs AgAgCl because of overpotential. Higher potentials may cause rapid fouling of electrodes, and additionally microbial cytochromes for example cytochrome a3 possess a reduction potential of around +0.385V vs SHE.

f) Keeping all conditions constant, repeated inoculations was performed until 27$^{th}$ subcultures (FIG. 5) or 10$^{th}$ subculture (FIG. 8), while at every subculture fresh medium was used.

g) In the scenario as shown in FIG. 5, after the 27$^{th}$ subculture, the inoculations continued up to 30$^{th}$ subculture as shown in FIG. 5. Alternatively, for example as shown in FIG. 8, after the 10$^{th}$ subculture, the inoculations were stopped.

One or more of the above steps can be used, as appropriate, in any of the methods of the invention as described herein.

The stepwise change of anti-oxidant/oxidized counterpart concentration ratio to adjust the redox state is according to the Nernst equation. Here follows an example for cysteine/cystine redox couple:

$$E_h = E_o\, RT/2F\ln([\text{Cystine}]/[\text{Cys}]^2) \quad (a)$$

Where:
$E_h$=redox potential=V
Eo=Standard redox potential of Cystine/Cysteine couple=0.25V at pH 7.4
R=General gas constant=8.31451 J K$^{-1}$ mol$^{-1}$
F=Faradays constant=96,485 C/mol
T=Absolute temperature (K)

The redox potential ($E_h$) values calculated for various concentrations of cysteine/cystine redox couple are presented in Table1.

TABLE 1

| Cysteine mM | Cystine | $E_h$ mV | |
|---|---|---|---|
| 7.2 | 0.4 | −223 | oxygen saturated medium |
| 7.995 | 0.005 | −283 | oxygen depleted growth |
| 7 | 1 | −211 | medium prepared by |
| 6 | 2 | −198 | nitrogen purging |
| 5 | 3 | −188 | |
| 4 | 4 | −178 | |
| 3 | 5 | −168 | |
| 2 | 6 | −155 | |
| 1 | 7 | −135 | |
| 0.01 | 8 | −13 | |

$$4R\text{—}SH + O_2 \rightarrow 2R\text{—}SS\text{—}R + H_2O \quad (b)$$

According to the equation (b), 4 moles of cysteine (R—SH) reacts with one mole of oxygen to produce 2 moles of cystine (R—SS—R).

The dissolved oxygen concentration in water at 25° C. is around 200 µM, and when the growth medium not purged with nitrogen prior to the experiment around 800 µM of cysteine will react with 200 µM of oxygen generating 400 µM of cystine. Thus for growth medium having 8 mM of cysteine an initial redox potential of around −223 mV will be observed. However, the complete degassing of oxygen in growth medium with oxygen free nitrogen provides a redox potential of around −283 mV, close to the gut luminal redox potential (around −300 mV)

The present invention further provides examples of adapted microorganisms that have been prepared by the methods of the present invention.

Thus, a yet further aspect of the invention provides a microorganism (adapted microorganism), e.g. a microorganism strain, obtained, obtainable, prepared, produced, identified or selected by the methods of the invention. Such strains can be a probiotic microorganism or bacterial strain. "Probiotic" as used herein refers to microorganisms that provide health benefits when consumed. For example, The Food and Agricultural Organization of the United Nations define probiotics as "live microorganisms which when administered in adequate amounts confer a health benefit on the host". Such microorganisms or strains can be isolated strains or pure cultures and will not correspond to naturally occurring microorganisms or strains as they have been subjected to the adaptation methods of the invention. Preferred microorganisms or strains are F. prausnitzii.

Examples of adapted strains obtained, etc., by the adaptation methods of the present invention are F. prausnitzii strains denoted herein as TCS1, OCS-1 and OCS-2. These strains have been deposited under the Budapest Treaty at DSMZ (Leibniz Institute DSMZ—German Collection of Microorganisms and Cell Cultures, Inhoffenstr. 7B, D-38124 Braunschweig, Germany) on Oct. 12, 2016 and have been given the accession numbers DSM 32380, DSM 32378 and DSM 32379, respectively.

The microorganisms or strains obtained, etc., by the methods of the invention (e.g. one or more of the deposited strains) may take the form of a compound (agent) or composition, e.g. a pharmaceutical compound or composition or a nutritional compound or composition.

The present invention thus also provides a composition or formulation comprising:

(i) a microorganism or strain, obtained, obtainable, prepared, produced, identified or selected by the method of the invention, or a microorganism or strain of the invention as otherwise defined herein (e.g. one or more of the deposited strains); and (ii) at least, one additional component selected from the group consisting of a carrier, diluent or excipient (e.g. a pharmaceutically acceptable carrier, diluent or excipient), a foodstuff or food supplement, or a further therapeutic or nutritional agent. Thus, said compositions can be formulated as pharmaceutical compositions or as nutritional compositions, e.g. as a food product.

Therapeutic uses of the microorganisms, strains, compositions and formulations of the invention as defined herein (e.g. one or more of the deposited strains), are also provided.

An appropriate mode of administration and formulation of the microorganisms, strains, compositions, formulations, etc., is chosen depending on the site of disease. A preferred mode of administration is oral or rectal, however, equally intravenous or intramuscular injection may be appropriate.

Appropriate doses of the microorganisms, strains, compositions and formulations of the invention as defined herein can readily be chosen or determined by a skilled person depending on the disorder to be treated, the mode of administration and the formulation concerned. For example, a dosage and administration regime is chosen such that the microorganisms, strains, compositions or formulations of the invention administered to a subject can result in a therapeutic or health benefit. For example, daily doses of microorganisms of $10^4$ to $10^{12}$, for example $10^5$ to $10^{10}$, or $10^6$ to $10^8$, or $10^8$ to $10^{10}$ total CFUs of bacteria may be used.

Thus, products or compositions or formulations or kits containing more oxygen tolerant anaerobic microorganisms obtained, etc., by the methods of the present invention or otherwise defined herein are provided. Advantageously, such products have increased shelf life or increased longer term storage.

Preferred products or compositions comprise frozen, freeze-dried, lyophilized, or dried bacteria (see also the Examples) and are preferably in a unit-dosage format, e.g. a capsule or tablet or gel. Appropriate doses (e.g. in the form of numbers of bacteria or CFUs) for use in such products, etc., are described elsewhere herein and in the Examples. Other components may also be included in such products, etc., for example preservatives (e.g. glycerol), stabilizers, gelling agents and/or cryoprotectants. In some embodiments such additional components are non-natural agents.

Where decreased (or reduced) concentrations, levels, or growth, is referred to herein, then preferably such decreases or reductions (and indeed other reductions or decreases or negative effects as mentioned elsewhere herein) are measurable decreases, more preferably they are significant decreases, preferably statistically significant decreases, for example with a probability value of ≤0.05, when compared to an appropriate control level or value.

Where increased (or elevated) concentrations, levels, voltage, tolerance or growth, etc., is referred to herein, e.g. stepwise increases, or increase in oxidative stress, oxygen flux (or diffusion or concentration), or oxygen tolerance, then preferably such increases (and indeed other increases or positive effects as mentioned elsewhere herein) are measurable increases, more preferably they are significant increases, preferably statistically significant increases, for example with a probability value of ≤0.05, when compared to an appropriate control level or value.

Indeed, where significant changes are described herein, it is preferred that such changes are statistically significant changes, for example with a probability value of ≤0.05, when compared to an appropriate control level or value.

The following are some examples of the invention, which are not meant to be limiting of the use of the invention herein but to show practical examples in detail of how the invention may be used.

EXAMPLES

Example 1

Adaptation of Anaerobic Microorganism to Oxidized Environment

Figure 6:
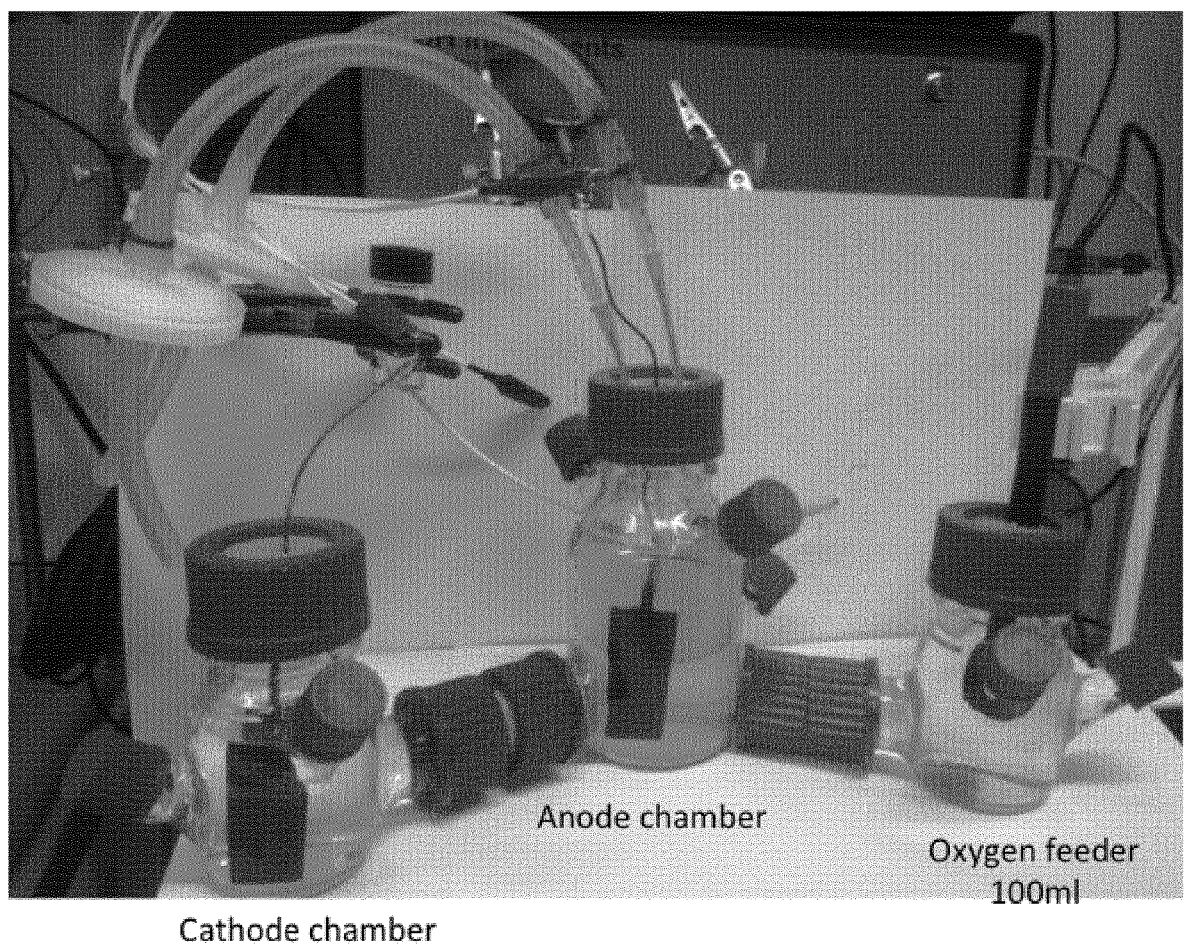
Figure 7:
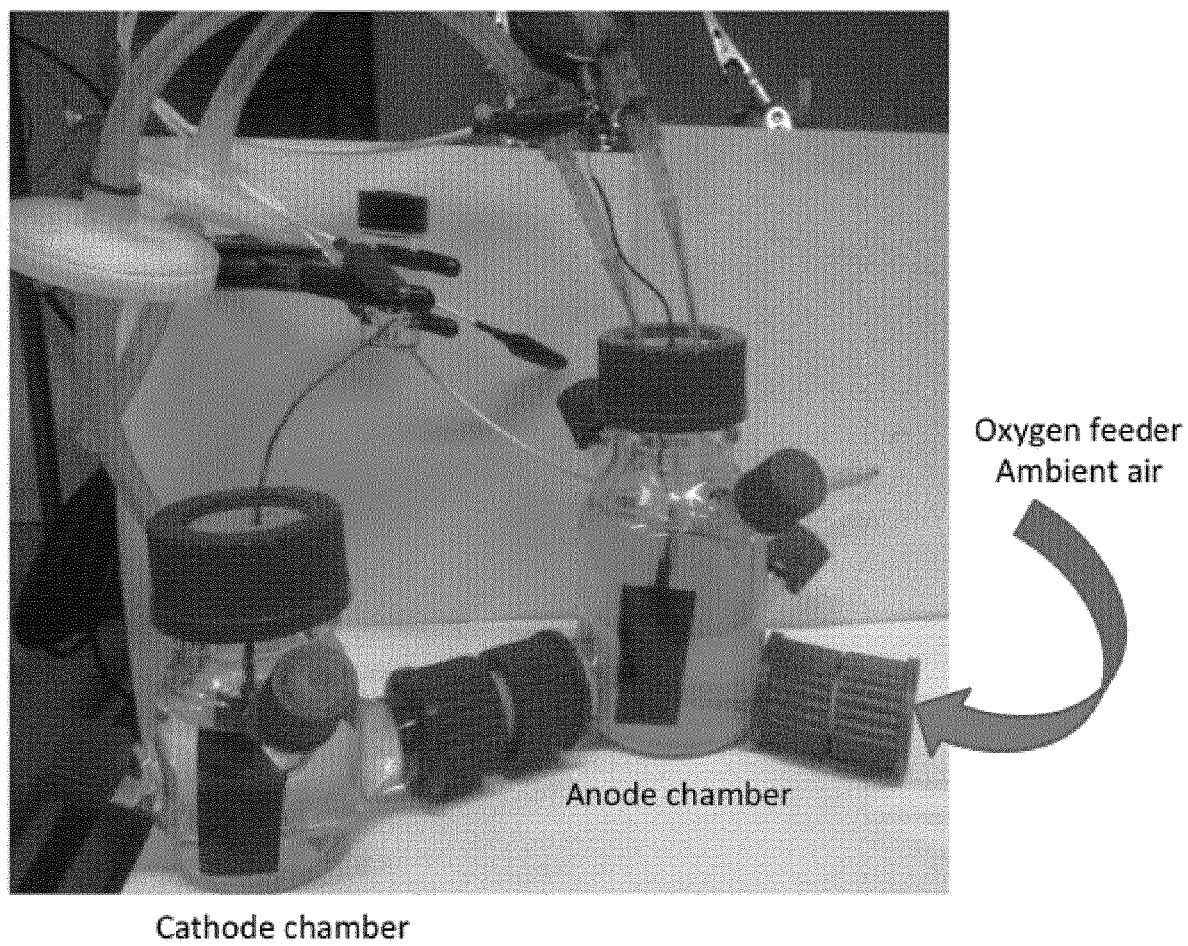

A *Faecalibacterium prausnitzii* strain was isolated from the feces of healthy volunteer by microbiological pure culture technique under strict anaerobic condition (5% $H_2$, 15% $CO_2$ and 80% $N_2$) employed in a Coy chamber and named FBT-22 (DSM 32186). (FBT-22 has been deposited under the Budapest Treaty at DSMZ (Leibniz Institute DSMZ—German Collection of Microorganisms and Cell Cultures, Inhoffenstr. 7B, D-38124 Braunschweig, Germany) on Oct. 20, 2015 and has been given the accession number DSM 32186). The routine culture medium used for isolation contains following (g/L); yeast extract: 2.5; casitone: 10; glucose: 4.5; sodium chloride: 0.9; dipotasium phosphate: 0.45; potassium dihydrogen phosphate: 0.45; ammonium sulfate: 1.32; sodium bicarbonate: 4g; cysteine: 1. resazurin: 0.001; hemin: 0.01. Vitamin mix contains: 10 μg biotin, 10 mg cobalamin, 30 μg p-aminobenzoic acid, 50 μg folic acid and 150 μg pyridoxamine. Final concentrations of short-chain fatty acids (SCFA) in the medium were 33 mM acetate, 9 mM propionate and 1 mM each of isobutyrate, isovalerate and valerate. All components were added aseptically while the tubes were flushed with $CO_2$. Heat labile vitamins were filter sterilized with 0.22 μm filter and added after the medium was autoclaved to give a final concentration of 0.05 μg thiamine $ml^{-1}$ and 0.05 μg riboflavin $ml^{-1}$. The final pH of the medium was adjusted with 1N NaOH or 1N HCl to 7.2±0.2. The media was autoclaved at 100 kPa at 121° C. for 15 mins. Cysteine was employed to simulate colonic redox potential of the growth medium and resazurin as redox indicator. Inoculum for the SHIRM bioreactor was prepared by inoculating single colony in 7 ml of culture medium. After 12 h-16 h of incubation at 37° C., culture reached the late exponential phase ($OD_{600}$~0.7). Two tubes of around 0.5 ml of the master culture was preserved in 20% glycerol at −80° C. and designated as FFR. These FFR stocks are designated as FFR-M1.1 and FFR-M1.2. FFRM1.1 was directly inoculated into 7 ml of the culture medium without thawing. Inoculums was incubated anaerobically for 12 h-16 h at 37° C. of incubation when the culture reached late exponential phase ($OD_{600}$~0.7), 2.5 ml of culture was inoculated in 250 ml SHIRM bioreactor. The proportion of this master culture was preserved in duplicates (as mentioned earlier) and designated as FFR-M2.1 and FFR-M2.2. In case of any contamination or mishap the experiment can be salvaged via corresponding FFRM cultures. The composition of SHIRM bed culture medium (SBCM) is same as used for primary isolation of strain FBT-22 (DSM 32186) however; later the cysteine concentration was decreased and balanced with equivalent amount of cystine. The applied electrical oxidizing potentials were maintained via external voltage on graphite anode (8.5 cm×0.25 cm×2.5 cm) via potentiostat. The cell circuit was completed by connecting cathode chamber to one side arm separated by proton exchange membrane. Oxygen flux was controlled by connecting oxygen feeder to the anode chamber separated via variable septum having different oxygen diffusion constants. The instantaneous oxygen flux was measured by Clark's type DO probe. The oxygen flux is controlled by purging oxygen feeder by pure oxygen, which diffuses into the anode chamber via semipermeable membrane. The diffusivities ($D_{Om}$) and the mass transfer constant ($K_{Om}$) of oxygen on the membrane are $2.4×10^{-6}$ $cm^2/s$ and $1.3×10^{-4}$ cm/s respectively. Additionally the oxygen flux was controlled by changing the bed volume of oxygen feeder for example 250 ml or 100 ml as shown in FIG. 6. The oxygen feeder can also be removed to allow direct diffusion of oxygen into the anode chamber as shown in FIG. 7. The agar mucin coating of the septum membrane further controls the oxygen diffusion to anode chamber. The agar mucin was prepared by dissolving and autoclaving following components (g/L): Agar: 2; NaCl: 8; KCl: 0.2; $Na_2HPO_4$: 1.42; $KH_2PO_4$: 0.24; Mucin type II: 5. The media was autoclaved at 100 kPa at 121° C. for 15 mins. The SHIRM contains SBCM, which was purged with oxygen free nitrogen for 15 mins to remove dissolve oxygen. The final cells concentration in SHIRM reactor was adjusted around $OD_{600}$~0.005. Then SBCM used for first inoculation with FFR-M2.1, was designated as SBCM $8.0/V_{0.1}$, where the former number ("8") indicates the cysteine concentration (mM) and the later number ("0") the cystine concentration (mM) and 'V' indicates the applied voltage vs Ag/AgCl. Every experiment will start with zero oxygen flux and oxygen diffuses from oxygen feeder at pre-defined constant rate. The SHIRM bioreactor was run for 24 h at 37° C. until the culture reached the stationary phase under an oxidizing potential of +100 mV.

The culture retrieved after first incubation was designated as "Population P1" which is around 5 generation old. The frozen stocks from this batch were referred as FFR-P1.1 and FFR-P1.2. The 2.5 ml of FFR-P1.1 was inoculated in new SHIRM reactor having SBCM 7.1/$V_{0.2}$. The reinoculations were continued until $6^{th}$ subculture yielding FFR-P6 and corresponding FFR-P were stored at each intermediate subculture. At this stage the cysteine concentration was reduced to 3 mM and cystine was increased to 5 mM while oxidizing potential was raised to 600 mV vs AgAgCl. At this stage the repeated inoculations were performed till $27^{th}$ subculture keeping all the conditions constant, while at every subculture fresh medium was used. After $27^{th}$ subculture, the inoculations continued up to $30^{th}$ subculture as shown in FIG. 5.

Example 2

Selection of Evolved Strain Adapted to Oxidative Environment

The various FFR-P from Example 1 are analyzed in order to select a strain adapted to oxidative environment and oxygen, which can be used for further production. The analysis is based on comparative metagenomics, metabolic characterization, growth kinetics, stability and tolerance.

The comparative metabolic characterization is performed via fatty acid profiling, more precisely butyrate production on various prebiotics such as inulin and resistant starch.

Comparative growth kinetics including biomass yields and growth rate are performed in normal culture mediums with or without bile salts and prebiotics.

The comparative stability and tolerance is conducted in the presence of simulated gastric fluid/simulated intestinal fluid with or without enzymes and exposures to ambient air for 30 min.

The simulated gastric fluid test solution (TS) is prepared according to United States Pharmacopeia (USP) guidelines by dissolving 2.0 g of sodium chloride and 3.2 g of purified pepsin (derived from porcine stomach mucosa, with an activity of 800 to 2500 units per mg of protein), in 7.0 mL of hydrochloric acid and water up to 1000 mL. This test solution has a pH of about 1.2.

Simulated Intestinal Fluid Test Solution (TS) USP is prepared by dissolving 6.8 g of monobasic potassium phosphate in 250 mL of water and then adding 77 mL of 0.2 N sodium hydroxide and 500 mL of water. 10.0 g of pancreatin is added and the resulting solution is adjusted with 0.2 N sodium hydroxide or 0.2 N hydrochloric acid to a pH of 6.8±0.1 and finally diluted to 1000 mL.

The microbial fuel cell and flavin-dependent reduction of 5,5'-dithiobis-2-nitrobenzoate was used to assess cytochrome expressions in FFR-M and FFR-P populations of cells while diaphorase activity was tested via nitro blue tetrazolium salt.

The best adapted strain is selected.

Example 3

Further Example of Adaptation of Anaerobic Microorganism to Oxidized Environment Following all the steps of Example 1 until the step of the culture retrieved after first incubation was designated as "Population P1" which is around 5 generation old. The frozen stocks from this batch were referred as FFR-P1.1 and FFR-P1.2. The 2.5 ml of FFR-P1.1 was inoculated in new SHIRM reactor having SBCM 7.1/$V_{0.2}$. The reinoculations were continued until $6^{th}$ subculture yielding FFR-P6 and corresponding FFR-P were stored at each intermediate subculture. At this stage the cysteine concentration was reduced to 3 mM and cystine was increased to 5 mM while oxidizing potential was raised to 600mVvsAgAgCl.

But in this Example 3 compared to Example 1, this stage of the repeated inoculations were performed till $10^{th}$ subculture in total, keeping all the conditions constant, while at every subculture fresh medium was used as shown in FIG. 8.

Example 4

Selection of Evolved Strain from Example 3

Figure 9:
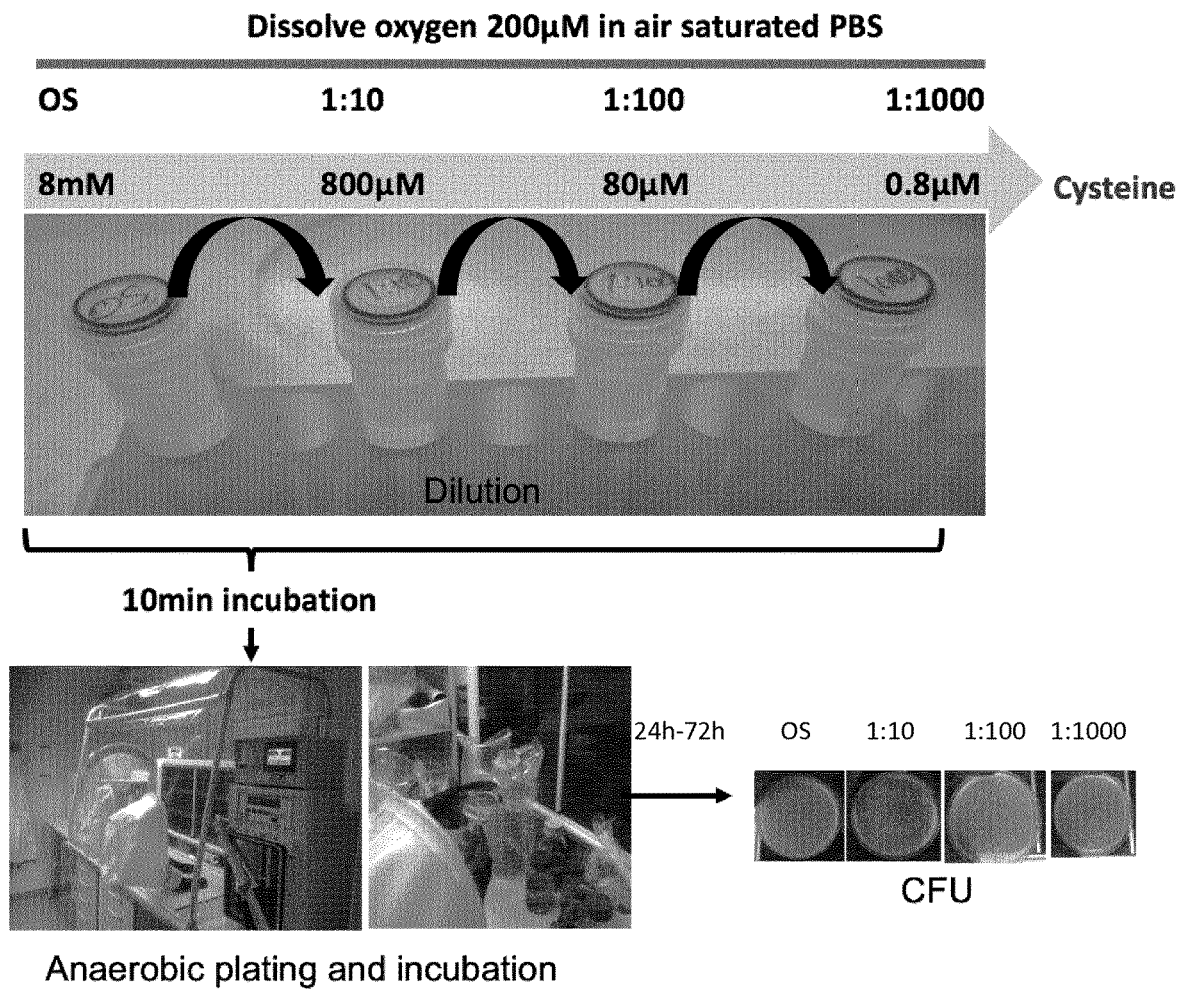
Figure 10:
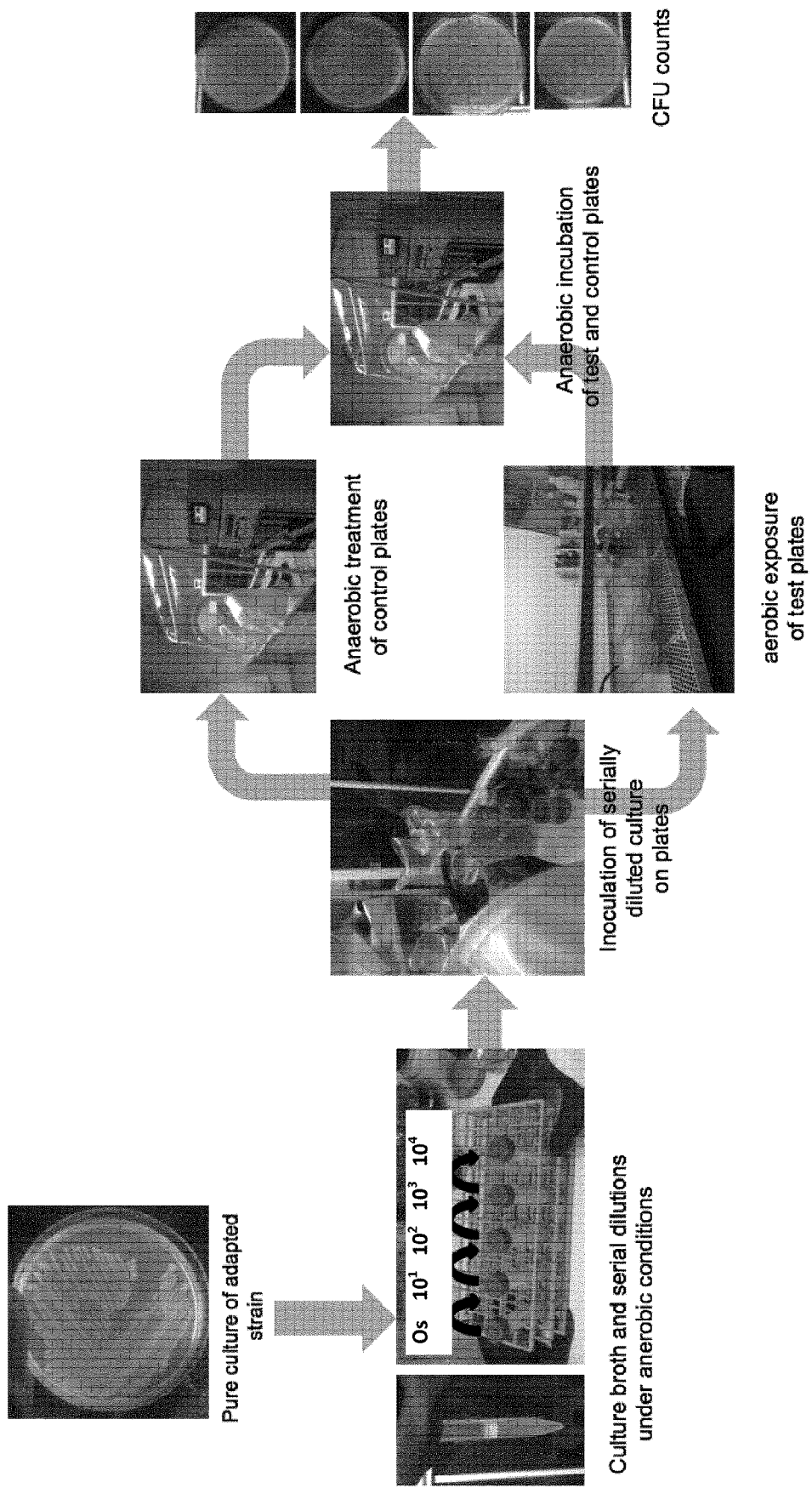

The various FFR-P from Example 3 are analyzed in order to select a strain adapted to oxidative environment and oxygen, which can be used for further production. The adapted strain selection is based on the following steps:

a. At every step shown in FIG. 8 an aliquot of 100 µl was collected.
b. Sample from 'step a' was serially diluted (up to $10^3$) in air saturated phosphate buffer saline (PBS) as shown in FIG. 9 and incubated in air tight vials at ambient temperature.
c. Vials were brought to anaerobic chamber and 50 µl aliquot was inoculated on YCFAG medium (Table 4).
d. Plates were incubated anaerobically for 24-72 h
e. After incubation, the viable counts were visually assessed.
f. Based on colony morphotype, any variant arisen after training were selected and purified via classical pure culture technique
g. The adapted strains were checked for purity via Gram staining
h. Five adapted strains selected from step-f were designated as TCS1, LTCS, STCS, OCS-1 and OCS-2.
i. The complete details of isolated adapted strains including respective isolation conditions and steps are presented in Table 2.
j. Preliminary identifications of adapted strains were based on Gram staining, metabolic phenotyping (short chain fatty acid profiles) and quantitative PCR (qPCR) using *F. prausnitzii* specific primers.
k. The strains identifications were confirmed via 16SrDNA sequencing.
l. The oxygen tolerance stability of the adapted strains was assessed as presented in FIG. 10. Respective adapted strains were anaerobically cultivated in YCFAG medium 12 h-14 h and serially diluted $10^1$, $10^2$, $10^3$, $10^4$ and/or $10^5$. Either 100 µl or 50 µl of serially diluted cultures were inoculated on YCFAG medium plates in duplicates. One set of plates incubated under anaerobic conditions and serve as control while other set was incubated aerobically for 20 mins. During 20 min exposure to ambient air, oxygen completely diffuses into the agar plate changing its color to pink. The redox indicator dye resazurin, which is colorless in reduced state, becomes pink after oxidation. This ensures the complete oxygen diffusion into the culture plate medium. After exposures to the respective treatments as depicted in FIG. 10 the test and control plates were incubated under anaerobic conditions for 48 h-72 h and viable counts were assessed visually.

m. After strain confirmation via 16SrDNA sequencing, adapted strains of *F. prausnitzii* TCS1, OCS-1 and OCS-2 were selected based on their oxygen tolerance and have been deposited under the Budapest Treaty at DSMZ (Leibniz Institute DSMZ—German Collection of Microorganisms and Cell Cultures, Inhoffenstr. 7B, D-38124 Braunschweig, Germany) and has been given the accession number DSM 32380, DSM 32378 and DSM 32379 respectively.

n. The oxygen tolerance of *F. prausnitzii* type strain, parental strain and adapted strains are depicted in Table 3.

TABLE 2 isolated adapted strains at different cycles

| | Strain code | Full name | Isolation condition |
|---|---|---|---|
| 1 | TCS1 | Translucent colonies smooth | 6$^{th}$ cycle of 3.5/V$_{0.6}$ (1:100) |
| 2 | LTCS | Large translucent colonies smooth | 10$^{th}$ cycle of 3.5/V$_{0.6}$ (1:1000) |
| 3 | STCS | Small translucent colonies smooth | 10$^{th}$ cycle of 3.5/V$_{0.6}$ (1:1000) |
| 4 | OCS-1 | Opaque colonies smooth | 10$^{th}$ cycle of 3.5/V$_{0.6}$ (1:10) |
| 5 | OCS-2 | Opaque colonies smooth | 10$^{th}$ cycle of 3.5/V$_{0.6}$ (1:10) |

TABLE 3 stability profiles of the adapted strains after exposure to air

| | Treatments | |
|---|---|---|
| | Anaerobic | Aerobic |
| Bacterial strains | CFU/ml | |
| *Faecalibacterium prausnitzii* A2-165 (DSM 17677) | 1.0E+08 | 0 |
| *Faecalibacterium prausnitzii* FBT-22 (DSM 32186) | 1.5E+07 | 0 |
| *Faecalibacterium prausnitzii* TCS1 (DSM 32380) | 7.0E+07 | 1.0E+03 |
| *Faecalibacterium prausnitzii* OCS1 (DSM 32378) | 6.5E+07 | 1.0E+05 |
| *Faecalibacterium prausnitzii* OCS2 (DSM32379) | 7.5E+07 | 7.0E+05 |

TABLE 4

YCFAG medium for *F. prausnitzii*

| | g/L | |
|---|---|---|
| Casitone | 10 | Autoclave together |
| Yeast extract | 2.5 | |
| NaCl | 0.9 | |
| K$_2$HPO$_4$ | 0.45 | |
| KH$_2$PO$_4$ | 0.45 | |
| NaHCO$_3$ | 4 | |
| CaCl$_2$•2H$_2$O | 0.12 | |
| MgSO$_4$•7H$_2$O | 0.09 | |
| Glucose | 4.5 | |
| Sodium acetate | 2.7 | |
| cysteine | 1 | |
| Ammonium sulfate | 1.32 | |
| Resazurin | 0.001 | |
| Hemin | 0.01 | |
| Vitamins | | |
| | µg/L | add After autoclave |
| Biotin (B7) | 10 | Filter sterilize |
| Cobalamin (B12) | 10 | |
| PABA | 30 | |
| Folic acid | 50 | |
| Pyridoxamine | 150 | |
| Riboflavin (B2) | 50 | |
| Thiamine (B1) | 50 | |
| SCFA | | |
| | mM | add After autoclave |
| propionate | 9 | Filter sterilize |
| isobutyrate | 1 | |
| isovalerate | 2 | |
| valerate | 3 | |
| Adjust final around pH 7.2 | | |

Example 5

Genetic Characterization of Evolved Strains

The evolved strains generated during every subculture in Example 1 are characterized by next generation sequencing (NGS). FFR-M and all FFR-P cultures are subjected to NGS for in-depth genomic analysis to unleash any possible mutations occurred in evolved/adapted FFR-P progeny. The differences between FFR-M and FFR-P strains are also studied at transcriptomic levels via RNA-seq.

Example 6

Enhanced Production of Anaerobic Microorganism

The production setup will involve optimized conditions obtained from Example 1. The culturing setup of the microorganism from Example 2 will be the same as in Example 1, but will involve only one step at fixed oxidizing conditions including voltage, cysteine/cystine couple and oxygen flux.

The optimized fermentation conditions are as follows; a membrane septum having mass transfer coefficient ($K_{Om}$) of oxygen $1.3 \times 10^{-4}$ cm/s and the oxygen diffusion rate into the anode chamber of around 0.2nmoles ml$^{-1}$min$^{-1}$, applied voltage 0.6V vsAgAgCL, cysteine 3 mM, cystine 5 mM and initial redox potential of growth medium SBCM around −188 mV.

The fermentation step is performed in a 150-liter electrically insulated vessel made of fluoropolymer based plastic material, in a triple chamber configuration. FIG. 4c. It is inoculated using the preparation as from Example 2 above.

The cell slurry from the fermentation is separated in a continuous centrifuge from Alfa Laval and mixed with standard cryoprotectants, as known in the art. A washing step is performed to avoid any freezing-point reduction in the freeze-drying process.

At the freeze-drying site the cell slurry is poured on each plate in the freeze dryer. The cell slurry of *Faecalibacterium prausnitzii* has a dry matter content of 18% and is freeze dried for four to five days.

Otherwise the fermentation and freeze-drying of the microorganism is done as known in the art.

The invention claimed is:

1. A method for producing anaerobic microorganisms adapted to increased oxygen tolerance, comprising:
(a) culturing anaerobic microorganisms under conditions comprising a stepwise dual induction of oxidative stress by (i) increasing in a stepwise manner an applied voltage and oxygen diffusion, and (ii) reducing in a stepwise manner the concentration of an antioxidant combined with increasing in a stepwise manner the concentration of an oxidized counterpart, thereby changing the anti-oxidant/oxidized counterpart concentration ratio and adjusting the redox state to produce adapted anaerobic microorganisms having increased oxygen tolerance; and (b) selecting the adapted anaerobic microorganisms.

2. The method of claim 1, wherein the anti-oxidant/oxidized counterpart is selected from the group consisting of cysteine/cystine, glutathione/glutathione-oxidized state, ascorbic acid/dehydroascorbate, dithiothreitol/oxidized dithiothreitol, and gallic acid/oxidized gallic acid.

3. The method of claim 1, wherein a starting condition for said method is a culture medium comprising (a) an oxygen concentration of zero to less than 50μM, (b) an applied voltage of zero, (c) a high concentration of the anti-oxidant, or (d) a low concentration of the oxidized counterpart, or any combination of (a)-(d).

4. The method of claim 3, wherein the starting condition is 8 mM cysteine, 0 mM cystine, an applied voltage of 0.1 V, an oxygen concentration of zero, or any combination thereof.

5. The method of claim 1, wherein when the antioxidant is cysteine and the anaerobic microorganisms are bacteria, the applied voltage does not exceed 0.6 V, the cysteine concentration is no lower than 3 mM, and/or the cysteine concentration is no higher than 5 mM, and/or a dissolved oxygen concentration in the culture medium is maintained at a sub-lethal concentration, whereby not all bacteria are killed.

6. The method of claim 3, wherein the oxygen concentration is less than 10μM.

7. The method of claim 3, wherein said starting conditions result in a redox potential corresponding to a gut luminal redox potential.

8. The method of claim 1, further comprising culturing the adapted anaerobic microorganisms from (a) under final conditions of applied voltage, oxygen diffusion and anti-oxidant/oxidized counterpart concentration ratio of (a).

9. The method of claim 1, wherein each step of increasing in (a)(i) and reducing and increasing in (a)(ii) comprises a reinoculation of the anaerobic microorganisms into a new culture medium, thereby producing the adapted anaerobic microorganisms.

10. The method of claim 1, wherein the anaerobic microorganisms are *Faecalibacterium prausnitzii*.

11. The method of claim 1 further comprising, determining oxygen tolerance, butyrate production, biomass yields and/or growth rate of the adapted anaerobic microorganisms.

* * * * *